US012642693B2

(12) United States Patent
Walker et al.

(10) Patent No.: US 12,642,693 B2
(45) Date of Patent: Jun. 2, 2026

(54) SELF-SEALING CONNECTOR FOR GEL PADS

(71) Applicant: C. R. Bard, Inc., Franklin Lakes, NJ (US)

(72) Inventors: Sean E. Walker, Platteville, CO (US); Audrey Earnshaw, Erie, CO (US); Angela Kontas, Denver, CO (US); Amy Lawrence, Port Orchard, WA (US); Brett R. Skelton, Louisville, CO (US); Ritaban Chakravarty, Louisville, CO (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 335 days.

(21) Appl. No.: 17/849,419

(22) Filed: Jun. 24, 2022

(65) Prior Publication Data

US 2023/0000668 A1 Jan. 5, 2023

Related U.S. Application Data

(60) Provisional application No. 63/218,001, filed on Jul. 2, 2021.

(51) Int. Cl.
*A61F 7/02* (2006.01)
*A61F 7/00* (2006.01)

(52) U.S. Cl.
CPC .............. *A61F 7/02* (2013.01); *A61F 7/0085* (2013.01); *A61F 2007/0054* (2013.01); *A61F 2007/0056* (2013.01); *A61F 2007/0277* (2013.01)

(58) Field of Classification Search
CPC .. A61F 7/0085; A61F 7/02; A61F 2007/0215; A61F 2007/0219;

(Continued)

(56) References Cited

U.S. PATENT DOCUMENTS 2,167,865 A     8/1939   Beecher
2,250,325 A     7/1941   Barnes
(Continued)

FOREIGN PATENT DOCUMENTS

AU          678753 B3      6/1997
AU       2007201161 B2     12/2010
(Continued)

OTHER PUBLICATIONS

Advantage Engineering, "Proper Use of Inhibited Propylene Glycol", Jun. 12, 2001, http://www.ttequip.com/knowledgelibrary/Proper%20Use%20Of%20Inh-ibited%20Propylene%20Glycol.pdf Jun. 12, 2001.

(Continued)

*Primary Examiner* — Joanne M Rodden
*Assistant Examiner* — Alyssa M Pape
(74) *Attorney, Agent, or Firm* — Rutan & Tucker LLP

(57) ABSTRACT

A targeted temperature management (TTM) system includes a TTM module configured to provide a TTM fluid and a pad configured to facilitate thermal energy transfer between the TTM fluid and a patient. The system includes a fluid delivery line (FDL) with a hub at the distal end of the FDL. The pad includes a connector including a flapper valve configured to alternate between open and closed positions based on whether the connector is coupled with the FDL hub. The flapper valve in the closed position covers openings of each of the fluid delivery conduit and fluid return conduit when the connector is uncoupled from the FDL hub. The flapper valve is configured to deform into the open position upon coupling of the connector and the FDL hub thereby establishing fluid communication therebetween.

21 Claims, 10 Drawing Sheets

(58) Field of Classification Search
CPC ...... A61F 2007/0225; A61F 2007/0054; A61F
2007/0056; A61F 2007/0277
See application file for complete search history.

(56) References Cited

U.S. PATENT DOCUMENTS

| | | |
|---|---|---|
| 2,296,207 A | 9/1942 | Kittinger |
| 2,595,328 A | 5/1952 | Bowen |
| 2,602,302 A | 7/1952 | Poux |
| 2,726,658 A | 12/1955 | Chessey |
| 2,807,809 A | 10/1957 | Kottemann |
| 3,075,529 A | 1/1963 | Young, Jr. |
| 3,091,242 A | 5/1963 | Johnson, Jr. et al. |
| 3,212,286 A | 10/1965 | Curtis |
| 3,506,013 A | 4/1970 | Zdenek |
| 3,734,293 A | 5/1973 | Biskis |
| 3,830,676 A | 8/1974 | Elkins |
| 3,867,939 A | 2/1975 | Moore et al. |
| 3,900,035 A | 8/1975 | Welch et al. |
| 3,927,671 A | 12/1975 | Chittenden et al. |
| 3,945,617 A | 3/1976 | Callery |
| 3,995,621 A | 12/1976 | Fletcher et al. |
| 4,059,293 A | 11/1977 | Sipler |
| 4,092,982 A | 6/1978 | Salem |
| 4,108,146 A | 8/1978 | Golden |
| 4,114,620 A | 9/1978 | Moore et al. |
| 4,118,946 A | 10/1978 | Tubin |
| 4,149,541 A | 4/1979 | Gammons et al. |
| 4,154,245 A | 5/1979 | Daily |
| 4,161,210 A | 7/1979 | Reid et al. |
| 4,195,631 A | 4/1980 | Baucom |
| 4,311,022 A | 1/1982 | Hall |
| 4,444,727 A | 4/1984 | Yanagihara et al. |
| 4,508,123 A | 4/1985 | Wyatt et al. |
| 4,580,408 A | 4/1986 | Stuebner |
| 4,753,241 A | 6/1988 | Brannigan et al. |
| 4,834,705 A | 5/1989 | Vaillancourt |
| 4,846,176 A | 7/1989 | Golden |
| 4,867,748 A | 9/1989 | Samuelsen |
| 4,884,304 A | 12/1989 | Elkins |
| 4,886,063 A | 12/1989 | Crews |
| 4,908,248 A | 3/1990 | Nakashima et al. |
| 4,919,134 A | 4/1990 | Streeter |
| 4,962,761 A | 10/1990 | Golden |
| 4,971,056 A | 11/1990 | Seacord |
| 4,981,135 A | 1/1991 | Hardy |
| 4,989,607 A | 2/1991 | Keusch et al. |
| 5,000,252 A | 3/1991 | Faghri |
| 5,005,374 A | 4/1991 | Spitler |
| 5,050,596 A | 9/1991 | Walasek et al. |
| 5,062,414 A | 11/1991 | Grim |
| 5,072,875 A | 12/1991 | Zacoi |
| 5,090,409 A | 2/1992 | Genis |
| 5,097,829 A | 3/1992 | Quisenberry |
| 5,111,668 A | 5/1992 | Parrish et al. |
| 5,113,666 A | 5/1992 | Parrish et al. |
| 5,133,348 A | 7/1992 | Mayn |
| 5,146,625 A | 9/1992 | Steele et al. |
| 5,154,706 A | 10/1992 | Cartmell et al. |
| 5,190,032 A | 3/1993 | Zacoi |
| 5,265,669 A | 11/1993 | Schneider |
| 5,268,022 A | 12/1993 | Garrett et al. |
| 5,289,695 A | 3/1994 | Parrish et al. |
| 5,300,103 A | 4/1994 | Stempel et al. |
| 5,304,213 A | 4/1994 | Berke et al. |
| 5,304,216 A | 4/1994 | Wallace |
| 5,320,164 A | 6/1994 | Szczesuil et al. |
| 5,329,638 A | 7/1994 | Hansen et al. |
| 5,383,919 A | 1/1995 | Kelly et al. |
| 5,393,462 A | 2/1995 | Avery |
| 5,405,366 A | 4/1995 | Fox et al. |
| 5,407,421 A | 4/1995 | Goldsmith |
| 5,409,500 A | 4/1995 | Dyrek |
| 5,411,541 A | 5/1995 | Bell et al. |
| 5,423,751 A | 6/1995 | Harrison et al. |
| 5,431,622 A | 7/1995 | Pyrozyk et al. |
| 5,437,673 A | 8/1995 | Baust et al. |
| 5,456,701 A | 10/1995 | Stout |
| 5,466,250 A | 11/1995 | Johnson, Jr. et al. |
| 5,470,353 A | 11/1995 | Jensen |
| 5,476,489 A | 12/1995 | Koewler |
| 5,484,448 A | 1/1996 | Steele et al. |
| 5,486,207 A | 1/1996 | Mahawili |
| 5,514,169 A | 5/1996 | Dickerhoff et al. |
| 5,545,194 A | 8/1996 | Augustine |
| 5,566,413 A | 10/1996 | Webb et al. |
| 5,605,144 A | 2/1997 | Simmons et al. |
| 5,609,620 A | 3/1997 | Daily |
| 5,620,482 A | 4/1997 | Augustine et al. |
| 5,624,477 A | 4/1997 | Armond |
| 5,634,940 A | 6/1997 | Panyard |
| 5,640,728 A | 6/1997 | Graebe |
| 5,645,855 A | 7/1997 | Lorenz |
| 5,658,325 A | 8/1997 | Augustine |
| 5,662,695 A | 9/1997 | Mason et al. |
| 5,683,439 A | 11/1997 | Jensen |
| 5,720,774 A | 2/1998 | Glucksman |
| 5,733,318 A | 3/1998 | Augustine |
| 5,755,755 A | 5/1998 | Panyard |
| 5,785,716 A | 7/1998 | Bayron et al. |
| 5,806,335 A | 9/1998 | Herbert et al. |
| 5,824,025 A | 10/1998 | Augustine |
| 5,837,002 A | 11/1998 | Augustine et al. |
| 5,840,080 A | 11/1998 | Der Ovanesian |
| 5,843,145 A | 12/1998 | Brink |
| 5,871,526 A | 2/1999 | Gibbs et al. |
| 5,879,378 A | 3/1999 | Usui |
| 5,887,437 A | 3/1999 | Maxim |
| 5,913,849 A | 6/1999 | Sundstrom et al. |
| 5,948,012 A | 9/1999 | Mahaffey et al. |
| 5,968,000 A | 10/1999 | Harrison et al. |
| 5,986,163 A | 11/1999 | Augustine |
| 5,989,285 A | 11/1999 | DeVilbiss et al. |
| 6,010,528 A | 1/2000 | Augustine et al. |
| 6,019,783 A | 2/2000 | Philips et al. |
| 6,030,412 A | 2/2000 | Klatz et al. |
| 6,047,106 A | 4/2000 | Salyer |
| 6,074,415 A | 6/2000 | Der Ovanesian |
| 6,083,256 A | 7/2000 | Der Ovanesian |
| 6,083,418 A | 7/2000 | Czarnecki et al. |
| 6,117,164 A | 9/2000 | Gildersleeve et al. |
| 6,176,869 B1 * | 1/2001 | Mason ..................... A61F 7/02 |
| | | 607/104 |
| 6,176,870 B1 | 1/2001 | Augustine |
| 6,185,744 B1 | 2/2001 | Poholski |
| 6,188,930 B1 | 2/2001 | Carson |
| 6,189,149 B1 | 2/2001 | Allen |
| 6,189,550 B1 | 2/2001 | Stickel et al. |
| 6,197,045 B1 | 3/2001 | Carson |
| 6,234,538 B1 | 5/2001 | Lauer |
| 6,238,427 B1 | 5/2001 | Matta |
| 6,255,552 B1 | 7/2001 | Cummings et al. |
| 6,257,011 B1 | 7/2001 | Siman-Tov et al. |
| 6,290,716 B1 | 9/2001 | Augustine |
| 6,336,935 B1 | 1/2002 | Davis et al. |
| 6,349,560 B1 | 2/2002 | Maier-Laxhuber et al. |
| 6,352,550 B1 | 3/2002 | Gildersleeve et al. |
| 6,364,937 B1 | 4/2002 | McMahon |
| 6,371,976 B1 | 4/2002 | Vrzalik et al. |
| 6,375,674 B1 | 4/2002 | Carson |
| 6,389,839 B1 | 5/2002 | Sabin |
| 6,436,130 B1 | 8/2002 | Philips et al. |
| 6,451,036 B1 | 9/2002 | Heitzmann et al. |
| 6,454,792 B1 | 9/2002 | Noda et al. |
| 6,461,379 B1 | 10/2002 | Carson et al. |
| 6,463,212 B1 | 10/2002 | Salyer |
| 6,503,297 B1 | 1/2003 | Lu et al. |
| 6,508,831 B1 | 1/2003 | Kushnir |
| 6,508,859 B1 | 1/2003 | Zia et al. |
| 6,511,501 B1 | 1/2003 | Augustine et al. |
| 6,511,502 B2 | 1/2003 | Fletcher |
| 6,517,510 B1 | 2/2003 | Stewart et al. |
| D471,987 S | 3/2003 | Hoglund et al. |
| D472,322 S | 3/2003 | Hoglund et al. |

(56)                  References Cited

U.S. PATENT DOCUMENTS

| | | | |
|---|---|---|---|
| 6,551,348 B1 | 4/2003 | Blalock et al. |
| D474,544 S | 5/2003 | Hoglund et al. |
| 6,559,096 B1 | 5/2003 | Smith et al. |
| 6,584,797 B1 | 7/2003 | Smith et al. |
| 6,589,270 B2 | 7/2003 | Augustine |
| 6,591,630 B2 | 7/2003 | Smith et al. |
| 6,601,404 B1 | 8/2003 | Roderick |
| 6,613,030 B1 | 9/2003 | Coles et al. |
| 6,620,187 B2 | 9/2003 | Carson et al. |
| 6,620,188 B1 | 9/2003 | Ginsburg et al. |
| 6,645,232 B2 | 11/2003 | Carson |
| 6,648,905 B2 | 11/2003 | Hoglund et al. |
| 6,653,607 B2 | 11/2003 | Ellis et al. |
| D483,125 S | 12/2003 | Hoglund et al. |
| 6,660,027 B2 | 12/2003 | Gruszecki et al. |
| 6,669,715 B2 | 12/2003 | Hoglund et al. |
| 6,682,525 B2 | 1/2004 | Lalonde et al. |
| D487,147 S | 2/2004 | Ellingboe et al. |
| D487,148 S | 2/2004 | Ellingboe et al. |
| 6,688,132 B2 | 2/2004 | Smith et al. |
| 6,692,518 B2 | 2/2004 | Carson |
| 6,699,267 B2 | 3/2004 | Voorhees et al. |
| 6,701,724 B2 | 3/2004 | Smith et al. |
| 6,743,250 B2 | 6/2004 | Renfro |
| 6,755,801 B2 | 6/2004 | Utterberg et al. |
| 6,755,852 B2 | 6/2004 | Lachenbruch et al. |
| D492,773 S | 7/2004 | Ellingboe et al. |
| 6,770,848 B2 | 8/2004 | Haas et al. |
| 6,799,063 B2 | 9/2004 | Carson |
| 6,800,087 B2 | 10/2004 | Papay et al. |
| 6,802,855 B2 | 10/2004 | Ellingboe et al. |
| 6,802,885 B2 | 10/2004 | Luk et al. |
| 6,818,012 B2 | 11/2004 | Ellingboe |
| 6,827,728 B2 | 12/2004 | Ellingboe et al. |
| 6,846,322 B2 | 1/2005 | Kane et al. |
| 6,858,068 B2 | 2/2005 | Smith et al. |
| 6,878,156 B1 | 4/2005 | Noda |
| 6,893,453 B2 | 5/2005 | Agarwal et al. |
| 6,904,956 B2 | 6/2005 | Noel |
| 6,909,074 B1 | 6/2005 | Bradley |
| 6,921,198 B2 | 7/2005 | Gruszecki et al. |
| 6,931,875 B1 | 8/2005 | Allen et al. |
| 6,942,644 B2 | 9/2005 | Worthen |
| 6,960,243 B1 | 11/2005 | Smith et al. |
| 6,968,711 B2 | 11/2005 | Smith et al. |
| 6,969,399 B2 | 11/2005 | Schock et al. |
| 7,008,445 B2 | 3/2006 | Lennox |
| 7,022,099 B2 | 4/2006 | Litzie et al. |
| 7,044,960 B2 | 5/2006 | Voorhees et al. |
| 7,052,509 B2 | 5/2006 | Lennox et al. |
| 7,055,575 B2 | 6/2006 | Noel |
| 7,056,335 B2 | 6/2006 | Agarwal et al. |
| 7,063,718 B2 | 6/2006 | Dobak, III |
| 7,077,858 B2 | 7/2006 | Fletcher et al. |
| 7,097,657 B2 | 8/2006 | Noda et al. |
| 7,101,389 B1 | 9/2006 | Augustine et al. |
| 7,122,047 B2 | 10/2006 | Grahn et al. |
| 7,160,316 B2 | 1/2007 | Hamilton et al. |
| 7,172,586 B1 | 2/2007 | Dae et al. |
| 7,240,720 B2 | 7/2007 | Noel |
| 7,303,554 B2 | 12/2007 | Alonde et al. |
| 7,303,579 B2 | 12/2007 | Schock et al. |
| 7,338,516 B2 | 3/2008 | Quincy, III et al. |
| 7,361,186 B2 | 4/2008 | Voorhees et al. |
| 7,377,935 B2 | 5/2008 | Schock et al. |
| 7,507,250 B2 | 3/2009 | Lennox |
| 7,517,360 B2 | 4/2009 | Frey et al. |
| RE40,815 E | 6/2009 | Kudaravalli et al. |
| 7,547,320 B2 | 6/2009 | Schook et al. |
| RE40,868 E | 8/2009 | Ryba et al. |
| 7,621,944 B2 | 11/2009 | Wilson et al. |
| 7,621,945 B2 | 11/2009 | Lennox et al. |
| 7,666,213 B2 | 2/2010 | Freedman, Jr. et al. |
| 7,678,716 B2 | 3/2010 | Yahiaoui et al. |
| 7,686,840 B2 | 3/2010 | Quincy, III et al. |
| 7,727,228 B2 | 6/2010 | Abboud et al. |
| 7,731,739 B2 | 6/2010 | Schock et al. |
| 7,744,640 B1 | 6/2010 | Faries, Jr. et al. |
| 7,749,261 B2 | 7/2010 | Hansen et al. |
| 7,763,061 B2 | 7/2010 | Schorr et al. |
| 7,771,461 B2 | 8/2010 | Schock et al. |
| 7,784,304 B2 | 8/2010 | Trinh et al. |
| 7,799,063 B2 | 9/2010 | Ingram et al. |
| 7,827,815 B2 | 11/2010 | Carson et al. |
| 7,867,266 B2 | 1/2011 | Collins |
| 7,892,269 B2 | 2/2011 | Collins et al. |
| 7,896,910 B2 | 3/2011 | Schirrmacher et al. |
| 7,918,243 B2 | 4/2011 | Diodati et al. |
| 8,047,010 B2 | 11/2011 | Carson et al. |
| 8,052,624 B2 | 11/2011 | Buchanan et al. |
| 8,066,752 B2 | 11/2011 | Hamilton et al. |
| 8,182,521 B2 | 5/2012 | Kane et al. |
| 8,187,697 B2 | 5/2012 | Quincy, III et al. |
| 8,216,163 B2 | 7/2012 | Edelman |
| 8,283,602 B2 | 10/2012 | Augustine et al. |
| 8,454,671 B2 | 6/2013 | Lennox et al. |
| D685,916 S | 7/2013 | Hoglund |
| 8,491,644 B1 | 7/2013 | Carson et al. |
| 8,597,217 B2 | 12/2013 | Lowe et al. |
| 8,597,339 B2 | 12/2013 | Augustine et al. |
| 8,603,150 B2 | 12/2013 | Kane et al. |
| 8,632,576 B2 | 1/2014 | Quisenberry |
| 8,647,374 B2 | 2/2014 | Koewler |
| 8,715,330 B2 | 5/2014 | Lowe et al. |
| 8,778,119 B2 | 7/2014 | Starr et al. |
| 8,808,344 B2 | 8/2014 | Scott et al. |
| 8,840,581 B2 | 9/2014 | McGill et al. |
| 9,034,458 B2 | 5/2015 | Li |
| 9,078,742 B2 | 7/2015 | Quincy, III et al. |
| 9,089,462 B1 | 7/2015 | Lafleche |
| 9,211,358 B2 | 12/2015 | Sinko et al. |
| 9,278,024 B2 | 3/2016 | Scott et al. |
| 9,333,112 B2 | 5/2016 | Carson |
| 9,433,527 B2 | 9/2016 | Varga et al. |
| 9,552,706 B2 | 1/2017 | Schneider, II et al. |
| 9,566,185 B2 | 2/2017 | Carson et al. |
| 9,622,907 B2 | 4/2017 | Carson et al. |
| 9,687,386 B2 | 6/2017 | Carson |
| 9,763,823 B2 | 9/2017 | Voorhees et al. |
| 9,907,889 B2 | 3/2018 | Locke et al. |
| 10,010,452 B2 | 7/2018 | Wenske et al. |
| 10,123,902 B2 | 11/2018 | Carson et al. |
| 10,220,198 B2 | 3/2019 | Fuchs et al. |
| 10,258,501 B2 | 4/2019 | Carson |
| 10,376,412 B2 | 8/2019 | Brienza et al. |
| 10,441,458 B2 | 10/2019 | Voorhees et al. |
| 10,441,707 B2 | 10/2019 | Voorhees et al. |
| 10,548,778 B2 | 2/2020 | Hassenpflug et al. |
| D887,426 S | 6/2020 | Matsushita |
| 10,912,672 B1 | 2/2021 | Jones et al. |
| D922,424 S | 6/2021 | Frueh et al. |
| D925,574 S | 7/2021 | Beko |
| D928,188 S | 8/2021 | Giannino et al. |
| 11,173,071 B1 | 11/2021 | Tawil et al. |
| D939,550 S | 12/2021 | Miyai et al. |
| 11,234,859 B2 | 2/2022 | Voorhees et al. |
| D947,216 S | 3/2022 | Leininger |
| 11,285,039 B2 | 3/2022 | Steele et al. |
| D948,534 S | 4/2022 | Bessette et al. |
| D952,666 S | 5/2022 | Sajan |
| D959,475 S | 8/2022 | Norman |
| D960,191 S | 8/2022 | Feit et al. |
| D973,067 S | 12/2022 | Oh et al. |
| 11,975,123 B2 | 5/2024 | Appel et al. |
| 2001/0034545 A1 | 10/2001 | Elkins |
| 2001/0039439 A1 | 11/2001 | Elkins et al. |
| 2002/0007203 A1 | 1/2002 | Gilmartin et al. |
| 2002/0015689 A1 | 2/2002 | Munro et al. |
| 2002/0107558 A1 | 8/2002 | Clifton et al. |
| 2002/0111657 A1 | 8/2002 | Dae et al. |
| 2002/0138121 A1 | 9/2002 | Fox |
| 2002/0161419 A1 | 10/2002 | Carson et al. |
| 2003/0074038 A1 | 4/2003 | Gruszecki et al. |
| 2003/0078638 A1 | 4/2003 | Voorhees et al. |

(56) References Cited

U.S. PATENT DOCUMENTS

| | | |
|---|---|---|
| 2003/0078639 A1 | 4/2003 | Carson |
| 2003/0078640 A1 | 4/2003 | Carson et al. |
| 2003/0109911 A1 | 6/2003 | Lachenbruch et al. |
| 2003/0114903 A1 | 6/2003 | Ellingboe |
| 2003/0135252 A1 | 7/2003 | MacHold et al. |
| 2003/0149359 A1 | 8/2003 | Smith |
| 2003/0149461 A1 | 8/2003 | Johnson |
| 2003/0150232 A1 | 8/2003 | Brudnicki |
| 2003/0163179 A1 | 8/2003 | Hoglund et al. |
| 2003/0163180 A1 | 8/2003 | Hoglund et al. |
| 2003/0163183 A1 | 8/2003 | Carson |
| 2003/0163185 A1 | 8/2003 | Carson |
| 2003/0212416 A1 | 11/2003 | Cinelli et al. |
| 2004/0030372 A1 | 2/2004 | Ellingboe et al. |
| 2004/0030373 A1 | 2/2004 | Ellingboe et al. |
| 2004/0059212 A1 | 3/2004 | Abreu |
| 2004/0064170 A1 | 4/2004 | Radons et al. |
| 2004/0064171 A1 | 4/2004 | Briscoe et al. |
| 2004/0073280 A1 | 4/2004 | Dae et al. |
| 2004/0082886 A1 | 4/2004 | Timpson |
| 2004/0087606 A1 | 5/2004 | Voorhees et al. |
| 2004/0133253 A1 | 7/2004 | Grahn et al. |
| 2004/0158303 A1 | 8/2004 | Lennox et al. |
| 2004/0225341 A1 | 11/2004 | Schock et al. |
| 2004/0243122 A1 | 12/2004 | Auth et al. |
| 2004/0252750 A1 | 12/2004 | Gruszecki et al. |
| 2004/0255362 A1 | 12/2004 | Soerens et al. |
| 2004/0260369 A1 | 12/2004 | Schock et al. |
| 2004/0267339 A1 | 12/2004 | Yon et al. |
| 2005/0028551 A1 | 2/2005 | Noda et al. |
| 2005/0060012 A1 | 3/2005 | Voorhees et al. |
| 2005/0065583 A1 | 3/2005 | Voorhees et al. |
| 2005/0096714 A1 | 5/2005 | Freedman et al. |
| 2005/0177212 A1 | 8/2005 | Njemanze |
| 2005/0187502 A1 | 8/2005 | Krempel et al. |
| 2005/0244629 A1 | 11/2005 | Usui et al. |
| 2005/0288749 A1 | 12/2005 | Lachenbruch |
| 2006/0024053 A1 | 2/2006 | Grant |
| 2006/0030916 A1 | 2/2006 | Lennox |
| 2006/0036304 A1 | 2/2006 | Cordani et al. |
| 2006/0058858 A1 | 3/2006 | Smith |
| 2006/0074469 A1 | 4/2006 | Lennox et al. |
| 2006/0122673 A1 | 6/2006 | Callister et al. |
| 2006/0124141 A1 | 6/2006 | Dobak |
| 2006/0136023 A1 | 6/2006 | Dobak |
| 2006/0161232 A1 | 7/2006 | Kasza et al. |
| 2006/0190066 A1 | 8/2006 | Worthen |
| 2006/0235114 A1 | 10/2006 | Kitazono et al. |
| 2006/0247744 A1 | 11/2006 | Nest et al. |
| 2006/0276089 A1 | 12/2006 | Amarasinghe et al. |
| 2006/0287697 A1* | 12/2006 | Lennox ................ A61F 7/0085 |
| | | 607/104 |
| 2006/0293734 A1 | 12/2006 | Scott et al. |
| 2007/0016270 A1 | 1/2007 | Stelea et al. |
| 2007/0043409 A1 | 2/2007 | Brian et al. |
| 2007/0049997 A1 | 3/2007 | Fields et al. |
| 2007/0054122 A1 | 3/2007 | Paisner et al. |
| 2007/0068931 A1 | 3/2007 | Augustine et al. |
| 2007/0073368 A1 | 3/2007 | Cazzini et al. |
| 2007/0100404 A1 | 5/2007 | Ko et al. |
| 2007/0173735 A1 | 7/2007 | Callister et al. |
| 2007/0213793 A1 | 9/2007 | Hayes |
| 2007/0225782 A1 | 9/2007 | Taylor |
| 2007/0244475 A1 | 10/2007 | Carson et al. |
| 2007/0270925 A1 | 11/2007 | Levinson |
| 2008/0027523 A1 | 1/2008 | Behringer et al. |
| 2008/0046046 A1 | 2/2008 | Ginsburg |
| 2008/0114431 A1 | 5/2008 | Ginsburg |
| 2008/0147152 A1 | 6/2008 | Quincy et al. |
| 2008/0249524 A1 | 10/2008 | Dunning |
| 2008/0255644 A1 | 10/2008 | Carson |
| 2008/0269852 A1 | 10/2008 | Lennox et al. |
| 2008/0275534 A1 | 11/2008 | Noel |
| 2009/0018504 A1 | 1/2009 | Pile-Spellman et al. |
| 2009/0043366 A1 | 2/2009 | Dae |

| | | |
|---|---|---|
| 2009/0066079 A1* | 3/2009 | Miros .................. F16L 37/248 |
| | | 285/124.5 |
| 2009/0088825 A1 | 4/2009 | Ota |
| 2009/0099629 A1 | 4/2009 | Carson et al. |
| 2009/0131835 A1 | 5/2009 | Voorhees et al. |
| 2009/0149925 A1 | 6/2009 | MacDonald et al. |
| 2009/0157000 A1 | 6/2009 | Waller |
| 2009/0177184 A1 | 7/2009 | Christensen et al. |
| 2009/0182400 A1 | 7/2009 | Dae et al. |
| 2009/0228082 A1 | 9/2009 | Ross, III et al. |
| 2009/0250367 A1 | 10/2009 | Murdoch et al. |
| 2009/0280182 A1 | 11/2009 | Beck et al. |
| 2009/0287283 A1 | 11/2009 | Biser et al. |
| 2009/0299287 A1 | 12/2009 | Carson et al. |
| 2009/0312823 A1 | 12/2009 | Patience et al. |
| 2009/0326619 A1 | 12/2009 | Kagan |
| 2010/0016933 A1 | 1/2010 | Chen et al. |
| 2010/0137951 A1 | 6/2010 | Lennox et al. |
| 2010/0168825 A1 | 7/2010 | Barbknecht |
| 2010/0198122 A1 | 8/2010 | Freund |
| 2010/0198320 A1 | 8/2010 | Pierre et al. |
| 2010/0204765 A1 | 8/2010 | Hall et al. |
| 2010/0217260 A1 | 8/2010 | Aramayo |
| 2010/0241073 A1* | 9/2010 | Andersen ................ A61M 5/44 |
| | | 604/113 |
| 2010/0312160 A1 | 12/2010 | Creighton et al. |
| 2010/0312202 A1 | 12/2010 | Henley et al. |
| 2011/0021960 A1 | 1/2011 | Filtvedt et al. |
| 2011/0029051 A1 | 2/2011 | Ross |
| 2011/0045056 A1 | 2/2011 | Munro et al. |
| 2011/0125238 A1 | 5/2011 | Nofzinger |
| 2011/0152982 A1 | 6/2011 | Richardson |
| 2011/0166633 A1 | 7/2011 | Stull |
| 2011/0172749 A1 | 7/2011 | Christensen et al. |
| 2011/0172750 A1 | 7/2011 | Cassidy et al. |
| 2011/0306972 A1 | 12/2011 | Widenhouse et al. |
| 2011/0307040 A1 | 12/2011 | Peterson |
| 2011/0308781 A1 | 12/2011 | O'Riordan et al. |
| 2011/0313497 A1 | 12/2011 | Mcfarlane |
| 2012/0046720 A1 | 2/2012 | Ishizaki |
| 2012/0065715 A1 | 3/2012 | Carson |
| 2012/0080031 A1 | 4/2012 | Belson |
| 2012/0095536 A1 | 4/2012 | Machold et al. |
| 2012/0172774 A1 | 7/2012 | Lowe et al. |
| 2012/0185021 A1 | 7/2012 | Johnson et al. |
| 2012/0191035 A1 | 7/2012 | Stephan |
| 2012/0204881 A1 | 8/2012 | Davidson et al. |
| 2012/0220960 A1 | 8/2012 | Ruland |
| 2012/0288848 A1 | 11/2012 | Latham et al. |
| 2013/0023808 A1 | 1/2013 | Brown et al. |
| 2013/0116760 A1 | 5/2013 | Carson et al. |
| 2013/0138185 A1 | 5/2013 | Paxman et al. |
| 2013/0190667 A1 | 7/2013 | Kane et al. |
| 2013/0238042 A1 | 9/2013 | Gildersleeve et al. |
| 2013/0238043 A1 | 9/2013 | Beardall et al. |
| 2013/0310725 A1 | 11/2013 | Jerrells et al. |
| 2014/0039451 A1 | 2/2014 | Bangera et al. |
| 2014/0046411 A1 | 2/2014 | Elkins et al. |
| 2014/0172050 A1 | 6/2014 | Dabrowiak |
| 2014/0214138 A1 | 7/2014 | Voorhees et al. |
| 2014/0222121 A1 | 8/2014 | Spence et al. |
| 2014/0228717 A1 | 8/2014 | Parish et al. |
| 2014/0228918 A1 | 8/2014 | Brienza et al. |
| 2014/0276253 A1 | 9/2014 | Varga et al. |
| 2014/0277301 A1 | 9/2014 | Varga et al. |
| 2014/0288621 A1 | 9/2014 | Efremkin |
| 2014/0316494 A1 | 10/2014 | Augustine et al. |
| 2014/0343639 A1 | 11/2014 | Hopper et al. |
| 2015/0025606 A1 | 1/2015 | Davis |
| 2015/0051673 A1 | 2/2015 | Rivas Tapia |
| 2015/0119963 A1 | 4/2015 | Cosse |
| 2015/0173942 A1 | 6/2015 | Whitely |
| 2015/0209192 A1 | 7/2015 | Manion et al. |
| 2015/0223972 A1 | 8/2015 | Dabrowiak |
| 2015/0230973 A1 | 8/2015 | Dabrowiak et al. |
| 2015/0250643 A1 | 9/2015 | Paradis |
| 2015/0290042 A1 | 10/2015 | Freer et al. |
| 2015/0366703 A1 | 12/2015 | Du |
| 2015/0373781 A1 | 12/2015 | Augustine et al. |

(56) References Cited

U.S. PATENT DOCUMENTS

| | | |
|---|---|---|
| 2016/0008166 A1 | 1/2016 | Voorhees et al. |
| 2016/0022477 A1 | 1/2016 | Schaefer et al. |
| 2016/0038336 A1 | 2/2016 | Hilton et al. |
| 2016/0310316 A1 | 10/2016 | Hixson, Jr. |
| 2016/0324683 A1 | 11/2016 | Carson |
| 2017/0049618 A1 | 2/2017 | Ward et al. |
| 2017/0135855 A1 | 5/2017 | Stefan et al. |
| 2017/0151087 A1 | 6/2017 | Carson et al. |
| 2017/0189225 A1 | 7/2017 | Voorhees et al. |
| 2017/0224528 A1 | 8/2017 | Berg et al. |
| 2017/0246029 A1 | 8/2017 | Clark |
| 2017/0246031 A1 | 8/2017 | Benyaminpour et al. |
| 2017/0246374 A1 | 8/2017 | Voorhees et al. |
| 2017/0348144 A1 | 12/2017 | Taylor et al. |
| 2017/0348145 A1 | 12/2017 | Voorhees et al. |
| 2017/0354534 A1 | 12/2017 | Paradis et al. |
| 2018/0000255 A1 | 1/2018 | Youngblood et al. |
| 2018/0014967 A1 | 1/2018 | Taylor |
| 2018/0042762 A1 | 2/2018 | Galer |
| 2018/0042763 A1 | 2/2018 | Galer et al. |
| 2018/0064594 A1 | 3/2018 | Finch, Jr. et al. |
| 2018/0140407 A1 | 5/2018 | Yoskowitz |
| 2018/0207024 A1 | 7/2018 | Dabrowiak et al. |
| 2018/0214297 A1 | 8/2018 | Hughett et al. |
| 2018/0214302 A1 | 8/2018 | Dabrowiak et al. |
| 2018/0263677 A1 | 9/2018 | Hilton et al. |
| 2018/0263748 A1 | 9/2018 | Quinn |
| 2018/0376539 A1 | 12/2018 | Augustine et al. |
| 2019/0083322 A1 | 3/2019 | Huang et al. |
| 2019/0085644 A1 | 3/2019 | Ames et al. |
| 2019/0099288 A1 | 4/2019 | Vergara et al. |
| 2019/0117446 A1 | 4/2019 | Carson et al. |
| 2019/0192337 A1 | 6/2019 | Taylor et al. |
| 2019/0201574 A1 | 7/2019 | Delury et al. |
| 2019/0262169 A1 | 8/2019 | Vergara et al. |
| 2019/0331277 A1 | 10/2019 | Vachon |
| 2020/0001022 A1 | 1/2020 | Landy, III et al. |
| 2020/0071051 A1 | 3/2020 | Lewis |
| 2020/0129326 A1 | 4/2020 | Sinha et al. |
| 2020/0155341 A1 | 5/2020 | Voorhees et al. |
| 2020/0214471 A1 | 7/2020 | Paperno |
| 2020/0246180 A1 | 8/2020 | Liang et al. |
| 2020/0345971 A1 | 11/2020 | Schirm et al. |
| 2020/0405530 A1 | 12/2020 | Taylor et al. |
| 2021/0060230 A1 | 3/2021 | Hopper et al. |
| 2022/0087874 A1 | 3/2022 | Schneider et al. |
| 2022/0151821 A1 | 5/2022 | Voorhees et al. |
| 2022/0192865 A1 | 6/2022 | Hughett, Sr. et al. |
| 2022/0192867 A1 | 6/2022 | Stich et al. |
| 2022/0233344 A1 | 7/2022 | Hoglund |
| 2022/0233347 A1 | 7/2022 | Canary et al. |
| 2022/0265468 A1 | 8/2022 | Xu et al. |
| 2022/0280336 A1 | 9/2022 | Smith et al. |
| 2022/0287875 A1 | 9/2022 | Minchew et al. |
| 2022/0287876 A1 | 9/2022 | Smith et al. |
| 2022/0296413 A1 | 9/2022 | Jones |
| 2022/0296414 A1 | 9/2022 | Bible et al. |
| 2022/0304847 A1 | 9/2022 | Kuroda et al. |
| 2022/0313478 A1 | 10/2022 | Johnston |
| 2022/0347009 A1 | 11/2022 | Hughett, Sr. et al. |
| 2022/0401259 A1 | 12/2022 | Basciano et al. |
| 2022/0406017 A1 | 12/2022 | Wang et al. |
| 2023/0009524 A1 | 1/2023 | Johnston et al. |
| 2023/0011631 A1 | 1/2023 | Yin et al. |
| 2023/0019048 A1 | 1/2023 | Stich et al. |
| 2023/0021245 A1 | 1/2023 | Walker et al. |
| 2023/0040583 A1 | 2/2023 | Falis et al. |
| 2023/0077318 A9 | 3/2023 | Voorhees et al. |
| 2023/0190519 A1 | 6/2023 | Stich et al. |
| 2024/0065884 A1 | 2/2024 | Fallows et al. |
| 2024/0082052 A1 | 3/2024 | Cho et al. |
| 2024/0091054 A1 | 3/2024 | Boone-Worthman et al. |
| 2024/0099878 A1 | 3/2024 | Voorhees et al. |
| 2024/0108497 A1 | 4/2024 | Daw et al. |
| 2024/0366422 A1 | 11/2024 | Johnston et al. |
| 2025/0032310 A1 | 1/2025 | Stich et al. |
| 2025/0041107 A1 | 2/2025 | Walker et al. |
| 2025/0110628 A1 | 4/2025 | Litman et al. |
| 2025/0134705 A1 | 5/2025 | Stich et al. |
| 2025/0143918 A1 | 5/2025 | Voorhees et al. |
| 2025/0161107 A1 | 5/2025 | Stich et al. |
| 2025/0198550 A1 | 6/2025 | Johnston et al. |
| 2025/0332025 A1 | 10/2025 | Brooks et al. |
| 2026/0026965 A1 | 1/2026 | Xu et al. |

FOREIGN PATENT DOCUMENTS

| | | |
|---|---|---|
| CA | 2729122 A1 | 7/2002 |
| CA | 2193385 C | 9/2006 |
| CN | 102026596 A | 4/2011 |
| CN | 101389372 B | 8/2012 |
| CN | 102746518 A | 10/2012 |
| CN | 103939695 B | 3/2016 |
| CN | 305928532 | 7/2020 |
| CN | 111643265 A | 9/2020 |
| CN | 306402573 | 3/2021 |
| CN | 113230017 A | 8/2021 |
| CN | 307690236 | 11/2022 |
| CN | 309180016 | 3/2025 |
| DE | 102014118510 A1 | 6/2016 |
| EP | 0862901 A1 | 9/1998 |
| EP | 1073388 A1 | 2/2001 |
| EP | 1616543 A2 | 1/2006 |
| EP | 1641503 A2 | 4/2006 |
| EP | 1718894 B1 | 7/2010 |
| EP | 2204150 A1 | 7/2010 |
| EP | 2269546 A1 | 1/2011 |
| GB | 2118440 A | 11/1983 |
| JP | H09508045 A | 8/1997 |
| JP | 2002-534160 A | 10/2002 |
| JP | 2007029638 A | 2/2007 |
| JP | 2013248293 A | 12/2013 |
| KR | 20110020420 A | 3/2011 |
| WO | 9807397 A1 | 2/1998 |
| WO | 98/31310 A1 | 7/1998 |
| WO | 199944552 A1 | 9/1999 |
| WO | 9953874 A1 | 10/1999 |
| WO | 2000040185 A1 | 7/2000 |
| WO | 2003086253 A2 | 10/2003 |
| WO | 2004075949 A2 | 9/2004 |
| WO | 2005028984 A1 | 3/2005 |
| WO | 2005117546 A2 | 12/2005 |
| WO | 2007120677 A2 | 10/2007 |
| WO | 2009/090403 A1 | 7/2009 |
| WO | 2009147413 A1 | 12/2009 |
| WO | 2009148636 A1 | 12/2009 |
| WO | 2012125916 A2 | 9/2012 |
| WO | 2012138980 A2 | 10/2012 |
| WO | 2015084925 A1 | 6/2015 |
| WO | 2016057119 A1 | 4/2016 |
| WO | 2016123500 A1 | 8/2016 |
| WO | 2017/127768 A1 | 7/2017 |
| WO | 2018075576 A1 | 4/2018 |
| WO | 2022/159879 A1 | 7/2022 |
| WO | 2022155130 A1 | 7/2022 |
| WO | 2022155132 A1 | 7/2022 |
| WO | 2022159513 A1 | 7/2022 |
| WO | 2022/165068 A1 | 8/2022 |
| WO | 2022235513 A1 | 11/2022 |
| WO | 2023121674 A1 | 6/2023 |
| WO | 2023140870 A1 | 7/2023 |
| WO | 2023154050 A1 | 8/2023 |
| WO | 2023229609 A1 | 11/2023 |

OTHER PUBLICATIONS

Hyperphysicis, "Thermal Conductivity", available Jul. 31, 2010, https://web.archive.org/web/20100731025127/http://hyperphysics. phy-astr.g- us.edu/hbase/tables.thrcn.html Jul. 31, 2010.

Murray, R. Z., et al. "Development and use of biomaterials as wound healing therapies" Burns & Trauma (2019) 7:2 https://doi. org/10.1186/s41038-018-0139-7 (2019).

(56)        References Cited

OTHER PUBLICATIONS

PCT/US2015/045548 filed Aug. 17, 2015 International Search Report and Written Opinion dated Novemeber 24, 2015.

Sevgi, M., et al. "Topical Antimicrobials for Burn Infections—An Update" Recent Pat Antiinfect Drug Discov. Dec. 2013; 8(3): 161-197.

Stoica, A. E., et al. "Hydrogel Dressings for the Treatment of Burn Wounds: An Up-To-Date Overview" Materials 2020, 13, 2853; doi:10.3390/ma13122853. (2020).

U.S. Appl. No. 15/512,025, filed Mar. 16, 2017 Final Office Action dated Jun. 25, 2020.

U.S. Appl. No. 15/512,025, filed Mar. 16, 2017 Non-Final Office Action dated Jul. 18, 2019.

U.S. Appl. No. 16/597,393, filed Oct. 9, 2019 Corrected Notice of Allowability dated Nov. 18, 2021.

U.S. Appl. No. 16/597,393, filed Oct. 9, 2019 Non-Final Office Action dated Apr. 28, 2021.

PCT/US2022/011980 filed Jan. 11, 2022 International Search Report and Written Opinion dated Apr. 13, 2022.

PCT/US2022/013007 filed Jan. 19, 2022 International Search Report and Written Opinion dated Apr. 22, 2022.

PCTUS2022011971 filed Jan. 11, 2022 International Search Report and Written Opinion dated Apr. 21, 2022.

U.S. Appl. No. 17/589,849, filed Jan. 31, 2022 Final Office Action dated Jun. 27, 2023.

U.S. Appl. No. 17/589,849, filed Jan. 31, 2022 Non-Final Office Action dated Apr. 12, 2023.

U.S. Appl. No. 17/589,849, filed Jan. 31, 2022 Notice of Allowance dated Aug. 23, 2023.

PCT/US2016/015688 filed Jan. 29, 2016 International Search Report and Written Opinion dated Apr. 1, 2016.

PCT/US2022/013672 filed Jan. 25, 2022, International Search Report and Written Opinion dated Jul. 15, 2022.

PCT/US2022/014147 filed Jan. 27, 2022 International Search Report and Written Opinion dated Jul. 18, 2022.

PCT/US2021/065144 filed Dec. 23, 2021 International Search Report dated Oct. 4, 2022.

PCT/US2022/026999 filed Apr. 29, 2022 International Search Report and Written Opinion dated Oct. 24, 2022.

U.S. Appl. No. 17/848,074, filed Jun. 23, 2022 Advisory Action dated Jul. 9, 2024.

U.S. Appl. No. 17/848,074, filed Jun. 23, 2022 Final Office Action dated Apr. 26, 2024.

U.S. Appl. No. 17/848,074, filed Jun. 23, 2022 Non-Final Office Action dated Nov. 30, 2023.

U.S. Appl. No. 18/536,087, filed Dec. 11, 2023 Non-Final Office Action dated Jun. 28, 2024.

PCT/US2022/013569 filed Jan. 24, 2022 International Search Report and Written Opinion dated Aug. 29, 2022.

PCT/US2022/016020 filed Feb. 10, 2022 International Search Report and Written Opinion dated Oct. 31, 2022.

US 17/547, 128 filed Dec. 9, 2021 Restriction Requirement dated Sep. 5, 2024.

U.S. Appl. No. 17/583,090, filed Jan. 24, 2022 Restriction Requirement dated Sep. 6, 2024.

U.S. Appl. No. 17/686,301, filed Mar. 3, 2022 Non-Final Office Action dated Oct. 1, 2024.

U.S. Appl. No. 17/689,791, filed Mar. 8, 2022 Restriction Requirement dated Oct. 16, 2024.

U.S. Appl. No. 17/691,990, filed Mar. 10, 2022 Restriction Requirement dated Oct. 16, 2024.

U.S. Appl. No. 17/709,019, filed Mar. 30, 2022 Restriction Requirement dated Oct. 16, 2024.

U.S. Appl. No. 17/723,210, filed Apr. 18, 2022 Restriction Requirement dated Oct. 16, 2024.

U.S. Appl. No. 17/848,074, filed Jun. 23, 2022 Non-Final Office Action dated Aug. 15, 2024.

U.S. Appl. No. 18/536,087, filed Dec. 11, 2023 Notice of Allowance dated Aug. 29, 2024.

U.S. Appl. No. 17/552,309, filed Dec. 15, 2021 Restriction Requirement dated Dec. 12, 2024.

U.S. Appl. No. 17/584,101, filed Jan. 25, 2022 Non-Final Office Action dated Feb. 5, 2025.

U.S. Appl. No. 17/584,101, filed Jan. 25, 2022 Restriction Requirement dated Nov. 5, 2024.

U.S. Appl. No. 17/686,301, filed Mar. 3, 2022 Final Office Action dated Jan. 29, 2025.

U.S. Appl. No. 17/689,791, filed Mar. 8, 2022 Non-Final Office Action dated Dec. 30, 2024.

U.S. Appl. No. 17/690,908, filed Mar. 9, 2022 Non-Final Office Action dated Dec. 18, 2024.

U.S. Appl. No. 17/691,990, filed Mar. 10, 2022 Non-Final Office Action dated Dec. 17, 2024.

U.S. Appl. No. 17/694,416, filed Mar. 14, 2022 Non-Final Office Action dated Jan. 22, 2025.

U.S. Appl. No. 17/694,416, filed Mar. 14, 2022 Restriction Requirement dated Nov. 8, 2024.

U.S. Appl. No. 17/700,216, filed Mar. 21, 2022 Non-Final Action dated Feb. 5, 2025.

U.S. Appl. No. 17/709,019, filed Mar. 30, 2022 Non-Final Office Action dated Dec. 31, 2004.

U.S. Appl. No. 17/723,210, filed Apr. 18, 2022 Non-Final Office Action dated Dec. 20, 2024.

U.S. Appl. No. 17/848,074, filed Jun. 23, 2022 Notice of Allowance dated Nov. 26, 2024.

All in 1: Injection Tracker, posted date unavailable [online], [retrieved Apr. 10, 2025]. Retrieved from internet, https://apps.apple.com/us/app/all-in-1-injection-tracker/id1667540577. (Year: 2025).

Creating an accessible, usable and compelling Injection Site Tracking feature that can used by all our users, posted date May 2020 [u online], [retrieved Apr. 10, 2025]. Retrieved from internet, https://www.bradstricker.com/case-studies/injection-site-tracking. (Year: 2020).

Injection Tracker App, posted date unavailable [online], [retrieved Apr. 10, 2025]. Retrieved from internet, https://www.vladcristei.com/project_page_it. (Year: 2025).

PCT/US2022/031428 filed May 27, 2022 International Search Report and Written Opinion dated Jan. 30, 2023.

U.S. Appl. No. 17/547,128, filed Dec. 9, 2021 Non-Final Office Action dated Feb. 10, 2025.

U.S. Appl. No. 17/552,309, filed Dec. 15, 2021 Non-Final Office Action dated Mar. 14, 2025.

U.S. Appl. No. 17/583,090, filed Jan. 24, 2022 Non-Final Office Action dated Feb. 13, 2025.

U.S. Appl. No. 17/678,965, filed Feb. 23, 2022 Non-Final Office Action dated Feb. 12, 2025.

U.S. Appl. No. 17/686,301, filed Mar. 3, 2022 Advisory Action dated Apr. 4, 2025.

U.S. Appl. No. 17/857,997, filed Jul. 5, 2022 Non-Final Office Action dated Apr. 28, 2025.

U.S. Appl. No. 17/857,997, filed Jul. 5, 2022 Restriction Requirement dated Feb. 12, 2025.

U.S. Appl. No. 17/859,995, filed Jul. 7, 2022 Non-Final Office Action dated Mar. 11, 2025.

U.S. Appl. No. 17/881,270, filed Aug. 4, 2022 Non-Final Office Action dated Apr. 28, 2025.

U.S. Appl. No. 17/881,270, filed Aug. 4, 2022 Restriction Requirement dated Feb. 11, 2025.

U.S. Appl. No. 29/939,277, filed Apr. 25, 2024 Non-Final Office Action dated May 13, 2025.

Wound care app can help determine appropriate wounddressings, posted date Apr. 24, 2013 [online], [retrieved Apr. 10, 2025]. Retrieved from internet, https://www.imedicalapps.com/2013/04/wound-care-app-dressings/. (Year: 2013).

Lustig et al. "Solute Diffusion in Swollen Membranes. IX. Scaling Laws for Solute Diffusion in Gels", Journal of Applied Polymer Science, vol. 36, pp. 735-747 (Year: 1988).

U.S. Appl. No. 17/547,128, filed Dec. 9, 2021 Advisory Action dated Nov. 19, 2025.

U.S. Appl. No. 17/552,309, filed Dec. 15, 2021 Advisory Action dated Oct. 2, 2025.

U.S. Appl. No. 17/552,309, filed Dec. 15, 2021 Non-Final Office Action dated Nov. 5, 2025.

(56)     References Cited

OTHER PUBLICATIONS

U.S. Appl. No. 17/583,090, filed Jan. 24, 2022 Notice of Allowance dated Sep. 30, 2025.
U.S. Appl. No. 17/584,101, filed Jan. 25, 2022 Final Office Action dated Oct. 23, 2025.
U.S. Appl. No. 17/686,301, filed Mar. 3, 2022 Final Office Action dated Oct. 28, 2025.
U.S. Appl. No. 17/689,791, filed Mar. 8, 2022 Non-Final Office Action dated Nov. 5, 2025.
U.S. Appl. No. 17/690,908, filed Mar. 9, 2022 Non-Final Office Action dated Oct. 2, 2025.
U.S. Appl. No. 17/694,416, filed Mar. 14, 2022 Non-Final Office Action dated Oct. 1, 2025.
U.S. Appl. No. 17/697,879, filed Mar. 17, 2022 Non-Final Office Action dated Sep. 30, 2025.
U.S. Appl. No. 17/700,216, filed Mar. 21, 2022 Advisory Action dated Oct. 9, 2025.
U.S. Appl. No. 17/700,216, filed Mar. 21, 2022 Non-Final Office Action dated Dec. 3, 2025.
U.S. Appl. No. 17/709,019, filed Mar. 30, 2022 Non-Final Office Action dated Nov. 19, 2025.
U.S. Appl. No. 17/837,956, filed Jun. 10, 2022 Non-Final Office Action dated Nov. 3, 2025.
U.S. Appl. No. 17/857,997, filed Jul. 5, 2022 Final Office Action dated Oct. 27, 2025.
U.S. Appl. No. 17/859,995, filed Jul. 7, 2022 Advisory Action dated Oct. 28, 2025.
U.S. Appl. No. 17/881,270, filed Aug. 4, 2022 Final Office Action dated Oct. 27, 2025.
U.S. Appl. No. 18/085,566, filed Dec. 20, 2022 Non-Final Office Action dated Oct. 1, 2025.
U.S. Appl. No. 18/273,163, filed Jul. 19, 2023 Restriction Requirement dated Nov. 6, 2025.
U.S. Appl. No. 18/274,156, filed Jul. 25, 2023 Non-Final Office Action dated Oct. 1, 2025.
U.S. Appl. No. 18/274,436, filed Jul. 26, 2023 Non-Final Office Action dated Oct. 1, 2025.
U.S. Appl. No. 18/289,341, filed Nov. 2, 2023 Restriction Requirement dated Nov. 6, 2025.
U.S. Appl. No. 29/939,277, filed Apr. 25, 2024 Restriction Requirement dated Oct. 2, 2025.
U.S. Appl. No. 17/547,128, filed Dec. 9, 2021 Final Office Action dated Aug. 27, 2025.
U.S. Appl. No. 17/552,309, filed Dec. 15, 2021 Final Office Action dated Jul. 30, 2025.
U.S. Appl. No. 17/583,090, filed Jan. 24, 2022 Final Office Action dated Jul. 1, 2025.
U.S. Appl. No. 17/678,965, filed Feb. 23, 2022 Notice of Allowance dated Jun. 3, 2025.
U.S. Appl. No. 17/686,301, filed Mar. 3, 2022 Non-Final Office Action dated May 14, 2025.
U.S. Appl. No. 17/689,791, filed Mar. 8, 2022 Advisory Action dated Jul. 24, 2025.
U.S. Appl. No. 17/689,791, filed Mar. 8, 2022 Final Office Action dated May 21, 2025.
U.S. Appl. No. 17/690,908, filed Mar. 9, 2022 Advisory Action dated Sep. 3, 2025.
U.S. Appl. No. 17/690,908, filed Mar. 9, 2022 Final Office Action dated Jun. 24, 2025.

U.S. Appl. No. 17/691,990, filed Mar. 10, 2022 Advisory Action dated Jul. 24, 2025.
U.S. Appl. No. 17/691,990, filed Mar. 10, 2022 Non-Final Office Action dated Aug. 28, 2025.
U.S. Appl. No. 17/694,416, filed Mar. 14, 2022 Advisory Action dated Aug. 20, 2025.
U.S. Appl. No. 17/694,416, filed Mar. 14, 2022 Final Office Action dated Jun. 20, 2025.
U.S. Appl. No. 17/700,216, filed Mar. 21, 2022 Final Office Action dated Jun. 23, 2025.
U.S. Appl. No. 17/709,019, filed Mar. 30, 2022 Advisory Action dated Jul. 24, 2025.
U.S. Appl. No. 17/709,019, filed Mar. 30, 2022 Final Office Action dated Jun. 15, 2025.
U.S. Appl. No. 17/723,210, filed Apr. 18, 2022 Advisory Action dated Jul. 31, 2025.
U.S. Appl. No. 17/723,210, filed Apr. 18, 2022 Final Office Action dated May 21, 2025.
U.S. Appl. No. 17/848,039, filed Jun. 23, 2021 Non-Final Office Action dated Jul. 29, 2025.
U.S. Appl. No. 17/859,995, filed Jul. 7, 2022 Final Office Action dated Aug. 22, 2025.
U.S. Appl. No. 18/085,566, filed Dec. 20, 2022 Restriction Requirement dated May 16, 2025.
U.S. Appl. No. 18/272,026, filed Jul. 12, 2023 Non-Final Office Action dated Jul. 31, 2025.
U.S. Appl. No. 17/686,301, filed Mar. 3, 2022 Advisory Action dated Jan. 14, 2026.
U.S. Appl. No. 17/691,990, filed Mar. 10, 2022 Final Office Action dated Mar. 9, 2026.
U.S. Appl. No. 17/697,879, filed Mar. 17, 2022 Non-Final Office Action dated Mar. 26, 2026.
U.S. Appl. No. 17/837,956, filed Jun. 10, 2022 Final Office Action dated Feb. 24, 2026.
U.S. Appl. No. 17/881,270, filed Aug. 4, 2022 Advisory Action dated Jan. 14, 2026.
U.S. Appl. No. 18/085,566, filed Dec. 20, 2022 Final Office Action dated Mar. 9, 2026.
U.S. Appl. No. 18/272,026, filed Jul. 12, 2023 Final Office Action dated Dec. 31, 2025.
U.S. Appl. No. 18/272,026, filed Jul. 12, 2023 Notice of Allowance dated Mar. 27, 2026.
U.S. Appl. No. 18/272,332, filed Jul. 13, 2023 Non-Final Office Action dated Mar. 25, 2026.
U.S. Appl. No. 18/272,332, filed Jul. 13, 2023 Restriction Requirement dated Jan. 21, 2026.
U.S. Appl. No. 18/273,163 filed Jul. 19, 2023 Non-Final Office Action dated Feb. 3, 2026.
U.S. Appl. No. 18/274,156 filed Jul. 25, 2023 Final Office Action dated Mar. 25, 2026.
U.S. Appl. No. 18/274,436, filed Jul. 26, 2023 Final Office Action dated Mar. 25, 2026.
U.S. Appl. No. 18/289,341, filed Nov. 2, 2023 Non-Final Office Action dated Feb. 18, 2026.
U.S. Appl. No. 18/715,504, filed May 31, 2024 Restriction Requirement dated Feb. 4, 2026.
U.S. Appl. No. 29/939,277, filed Apr. 25, 2024 Ex Parte Quayle Action dated Feb. 23, 2026.

* cited by examiner

SELF-SEALING CONNECTOR FOR GEL PADS

PRIORITY

This application claims the benefit of priority to U.S. Provisional Application No. 63/218,001, filed Jul. 2, 2021, which is incorporated by reference in its entirety into this application.

BACKGROUND

The effect of temperature on the human body has been well documented and the use of targeted temperature management (TTM) systems for selectively cooling and/or heating bodily tissue is known. Elevated temperatures, or hyperthermia, may be harmful to the brain under normal conditions, and even more importantly, during periods of physical stress, such as illness or surgery. Conversely, lower body temperatures, or mild hypothermia, may offer some degree of neuroprotection. Moderate to severe hypothermia tends to be more detrimental to the body, particularly the cardiovascular system.

Targeted temperature management can be viewed in two different aspects. The first aspect of temperature management includes treating abnormal body temperatures, i.e., cooling the body under conditions of hyperthermia or warming the body under conditions of hypothermia. The second aspect of thermoregulation is an evolving treatment that employs techniques that physically control a patient's temperature to provide a physiological benefit, such as cooling a stroke patient to gain some degree of neuroprotection. By way of example, TTM systems may be utilized in early stroke therapy to reduce neurological damage incurred by stroke and head trauma patients. Additional applications include selective patient heating/cooling during surgical procedures such as cardiopulmonary bypass operations.

TTM systems circulate a fluid (e.g., water) through one or more thermal contact pads coupled with a patient to affect surface-to-surface thermal energy exchange with the patient. In general, TTM systems comprise a TTM fluid control module coupled with at least one thermal contact pad via a fluid delivery line. In some embodiments, tubing extends from a thermal contact pad to couple with the fluid delivery line. One such TTM system is disclosed in U.S. Pat. No. 6,645,232, titled "Patient Temperature Control System with Fluid Pressure Maintenance" filed Oct. 11, 2001, and one such thermal contact pad and related system is disclosed in U.S. Pat. No. 6,197,045 titled "Cooling/heating Pad and System" filed Jan. 4, 1999, both of which are incorporated herein by reference in their entireties. As noted in the '045 patent, the ability to establish and maintain thermally intimate pad-to-patient contact is of importance to fully realizing medical efficacies with TTM systems.

A fluid delivery line generally includes at least two fluid conduits for transporting TTM fluid to and from the thermal contact pad. Fluid delivery lines may include connection systems for selectively connecting to and disconnecting from the thermal contact pad. Although TTM systems may include a functionality to purge a thermal contact pad prior to disconnecting the thermal contact pad from a fluid delivery line, an operator may fail to utilize such functionality and, even when utilized, such functionality may leave some TTM fluid in the thermal contact pad. As a result, upon disconnection, some TTM fluid may leak from the tubing extending from the thermal connection pad thereby causing health and safety risks. Disclosed herein are systems, devices, and methods for preventing leakage of TTM fluid upon disconnecting a thermal contact pad from a fluid delivery line.

SUMMARY OF THE INVENTION

Briefly summarized, disclosed herein is a targeted temperature management (TTM) pad to receive and circulate TTM fluid to facilitate thermal energy transfer between the TTM fluid and a patient, the TTM pad including a pad portion configured for placement on the patient, a fluid delivery conduit extending away from the pad portion, the fluid delivery conduit including a delivery conduit connector at a proximal end thereof, a fluid return conduit extending away from the pad portion, the fluid return conduit including a return conduit connector at a proximal end thereof, and a connector coupled to a distal end of each of the fluid delivery conduit and the fluid return conduit, the connector including a flapper valve configured to alternate between open and closed positions based on whether the connector is coupled with a fluid delivery line (FDL) hub. The connector includes a connector housing having disposed therein proximal ends of the fluid delivery conduit and the fluid return conduit, a conduit partition separates the fluid delivery conduit and fluid return conduit and the flapper valve.

The flapper valve is configured in the closed position covering openings of each of the fluid delivery conduit and fluid return conduit when the connector is uncoupled from the FDL hub. The connector is configured to receive the FDL hub upon coupling (connecting) causing the flapper valve to deform into the open position, wherein coupling the connector and the FDL hub establishes fluid communication therebetween. The flapper valve is configured to deform around the conduit partition. In some embodiments, the conduit partition includes an aperture, and wherein the flapper valve is disposed in the aperture. In some such embodiments, wherein each of a proximal side and a distal side of the aperture includes tapering to facilitate deformation of the flapper valve upon coupling of the connector and the FDL hub.

In some embodiments, the connector includes a top compression strip connected to a top latch and a bottom compression strip connected to a bottom latch, wherein each of the top latch and bottom latch extends proximally from the connector. The top and bottom compression strips are configured to cause movement of the top and bottom latches in opposing directions upon application of pressure to the top and bottom compressions strips. Upon coupling of the connector and the FDL hub, an opening of the fluid delivery conduit is configured to receive a distal conduit tip of the fluid delivery lumen and an opening of the fluid return conduit is configured to receive a distal conduit tip of the fluid return lumen.

Also discussed herein is a targeted temperature management (TTM) system, comprising a TTM module configured to provide a TTM fluid, a fluid delivery line (FDL) including a FDL hub, a fluid delivery lumen and a fluid return lumen, and a pad discussed above. Further, embodiments of a method of exchanging thermal energy with a patient are disclosed, where the method comprises providing a targeted temperature management (TTM) module configured to circulate TTM fluid through one or more pads, the TTM module including a fluid delivery line (FDL) for transporting TTM fluid to and from the one or more pads, the FDL including an FDL hub, a fluid delivery lumen and a fluid return lumen, providing a pad as discussed above, connecting the delivery conduit connector and the return conduit connector to the FDL hub to establish fluid communication of the fluid delivery conduit and the fluid return conduit with the FDL, applying the pad portion to the patient, and initiating circulation of the TTM fluid through the pad.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Figure 1:
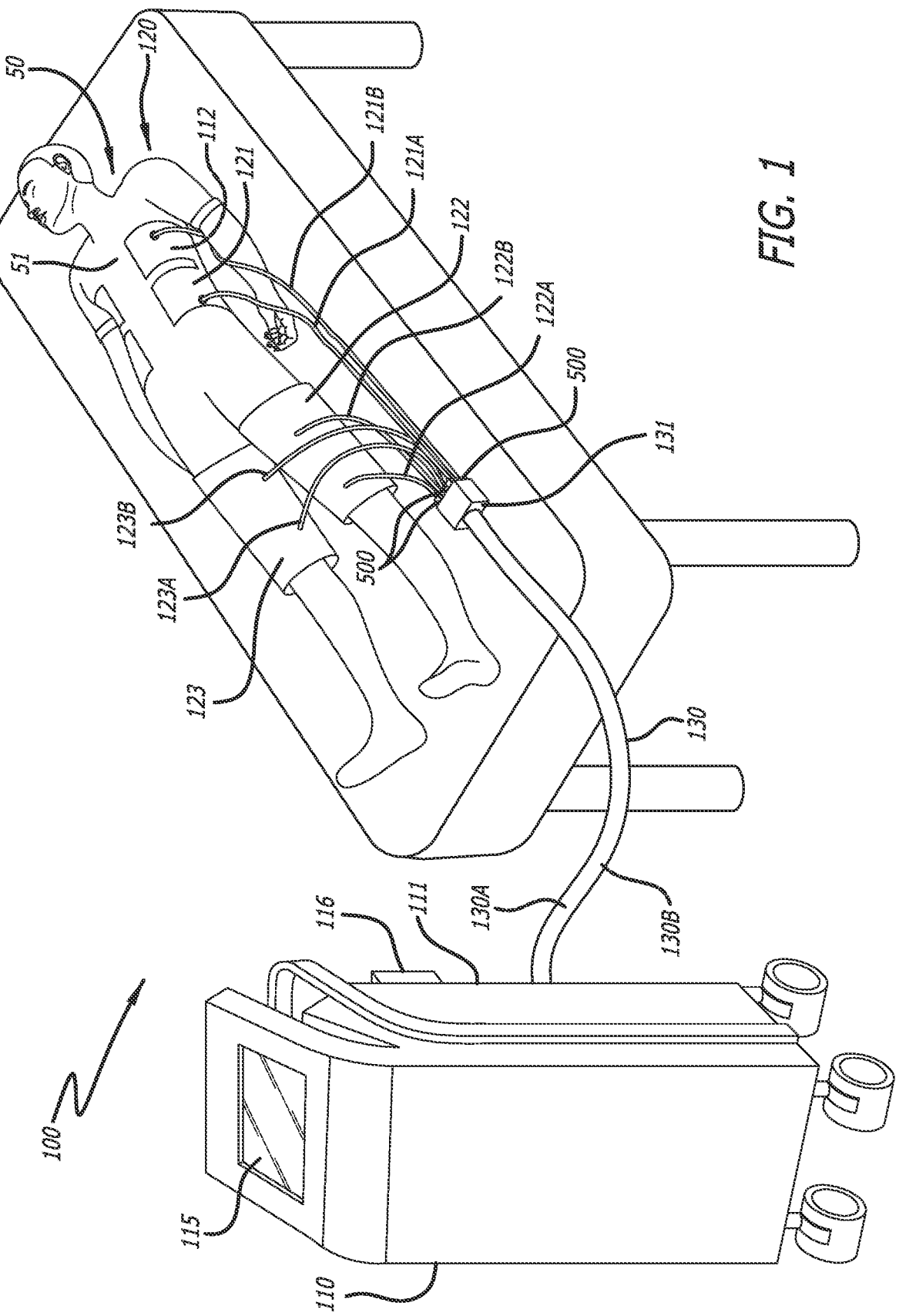
FIG. 1 illustrates a targeted temperature management (TTM) system for cooling or warming a patient, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," "horizontal," "vertical" and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. The words "including," "has," and "having," as used herein, including the claims, shall have the same meaning as the word "comprising." Furthermore, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The phrases "connected to" and "coupled with" refer to any form of interaction between two or more entities, including mechanical, electrical, magnetic, electromagnetic, fluid, signal, communicative (including wireless), and thermal interaction. Two components may be connected to or coupled with each other even though they are not in direct contact with each other. For example, two components may be coupled with each other through an intermediate component.

The directional terms "proximal" and "distal" are used herein to refer to opposite locations on a medical device. The proximal end of the device is defined as the end of the device closest to the end-user when the device is in use by the end-user. The distal end is the end opposite the proximal end, along the longitudinal direction of the device, or the end furthest from the end-user.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Unless defined otherwise, all technical and scientific terms used herein have the same meaning as commonly understood by those of ordinary skill in the art.

FIG. 1 illustrates a targeted temperature management (TTM) system 100 connected to a patient 50 for administering TTM therapy to the patient 50, where the therapy may include a cooling and/or warming of the patient 50, in accordance with some embodiments. The TTM system 100 includes a TTM module 110, a fluid delivery line (FDL) 130, and a thermal contact pad set 120. In the illustrated embodiment, the pad set 120 includes three thermal contact pads (pads) 121, 122, 123. In other embodiments, the pad set 120 may include one or more thermal contact pads (e.g., any number of pads). In the illustrated embodiments, the FDL 130 is configured to couple with two thermal pads. In other embodiments, the FDL 130 may be configured to couple with one or more thermal contact pads. In some embodiments, the system 100 may include more than one FDL 130.

Each pad includes a fluid delivery conduit and a fluid return conduit (sometimes referred to generally as the fluid conduits) coupled with the FDL 130 via an FDL hub 131. The FDL 130 includes a fluid delivery lumen 130A and a fluid return lumen 130B. In the illustrated embodiment, the pad 121 includes the fluid delivery conduit 121A coupled with the FDL 130 so as to be in fluid communication with the fluid delivery lumen 130A and a fluid return conduit 121B coupled with the FDL 130 so as to be in fluid communication with the fluid return lumen 130B. Similarly, the pad 122 includes the fluid delivery conduit 122A coupled with the FDL 130 so as to be in fluid communication with the fluid delivery lumen 130A and a fluid return conduit 122B coupled with the FDL 130 so as to be in fluid communication with the fluid return lumen 130B. Further, the pad 123 includes the fluid delivery conduit 123A coupled with the FDL 130 so as to be in fluid communication with the fluid delivery lumen 130A and a fluid return conduit 123B coupled with the FDL 130 so as to be in fluid communication with the fluid return lumen 130B. The proximal ends of the conduits 121A, 121B, the conduits 122A, 122B, and the conduits 123A, 123B may each terminate at a pad connector 500 discussed in detail below.

In use, the TTM module 110 prepares the TTM fluid 112 for delivery to the pad set 120 by heating or cooling the TTM fluid 112 to a defined temperature in accordance with prescribed TTM therapy parameters input by clinician via a graphical user interface 115. The TTM module 110 circulates the TTM fluid 112 between the TTM module 110 and the pad set 120 via the FDL 130. The pad set 120 is applied to the skin 51 of the patient to facilitate thermal energy exchange between the pad set 120 and the patient 50. During the TTM therapy, the TTM module 110 may continually control the temperature of the TTM fluid 112 toward a target temperature. The TTM module 110 may further include a pad identification interface 116 as further described below in relation to FIG. 3

Figure 2:
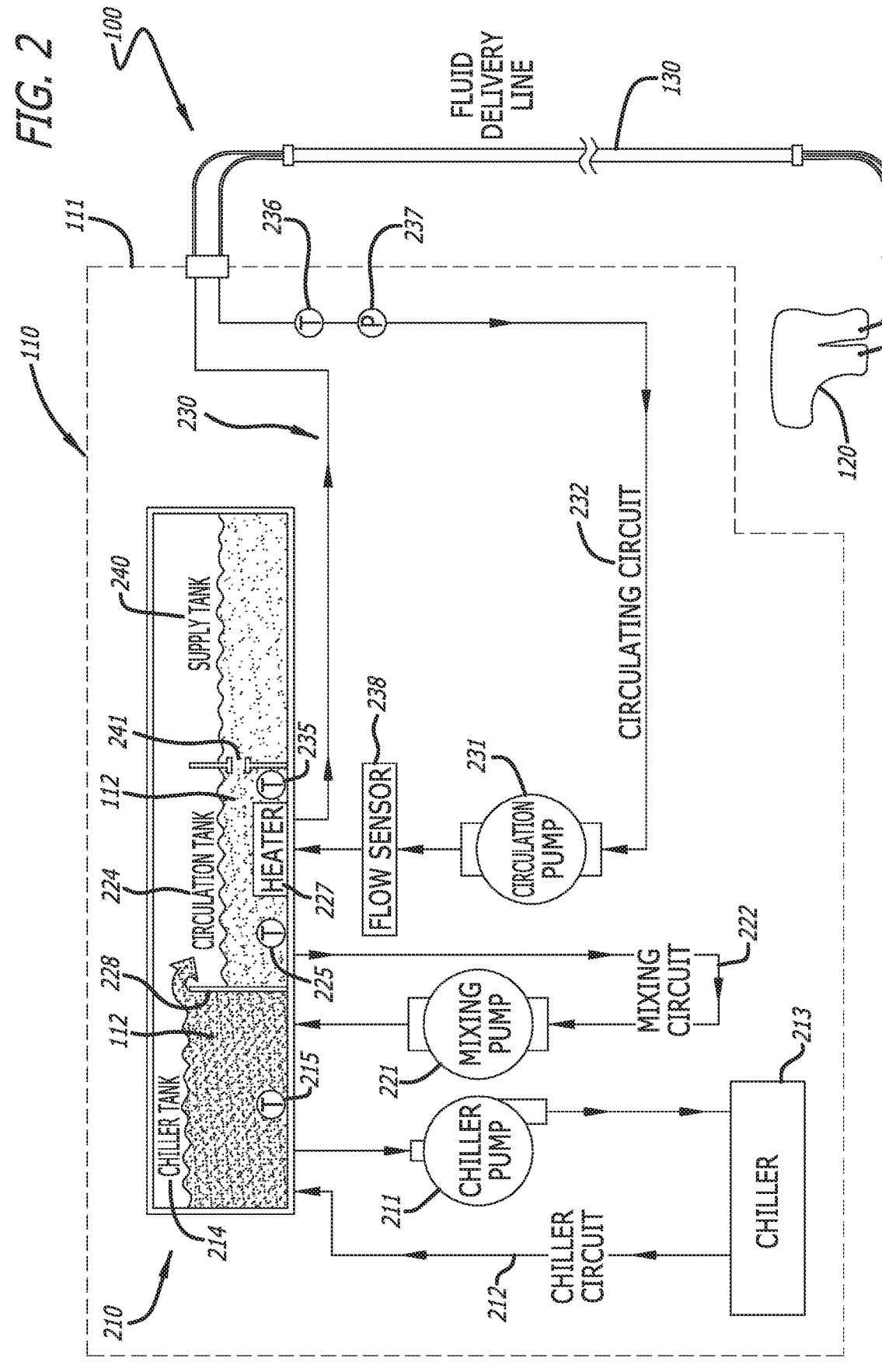
FIG. 2 illustrates a hydraulic schematic of the TTM system of FIG. 1, in accordance with some embodiments.

FIG. 2 illustrates a hydraulic schematic of the TTM system 100. The pad set 120 (FIG. 1) along with the corresponding fluid conduits are disposed external to the housing 111 of the TTM module 110. The TTM module includes various fluid sensors and fluid control devices to prepare and circulate the TTM fluid 112. The fluid subsystems of the TTM module may include a temperature control subsystem 210 and a circulation subsystem 230.

The temperature control subsystem 210 may include a chiller pump 211 to pump (recirculate) TTM fluid 112 through a chiller circuit 212 that includes a chiller 213 and a chiller tank 214. A temperature sensor 215 within the chiller tank 214 is configured to measure a temperature of the TTM fluid 112 within the chiller tank 214. The chiller 213 may be controlled by a temperature control logic (see FIG. 3) as further described below to establish a desired temperature of the TTM fluid 112 within chiller tank 214. In some instances, the temperature of the TTM fluid 112 within the chiller tank 214 may be less than the target temperature for the TTM therapy.

The temperature control subsystem 210 may further include a mixing pump 221 to pump TTM fluid 112 through a mixing circuit 222 that includes the chiller tank 214, a circulation tank 224, and a dam 228 disposed between the chiller tank 214 and circulation tank 224. The TTM fluid 112, when pumped by the mixing pump 221, enters the chiller tank 214 and mixes with the TTM fluid 112 within the chiller tank 214. The mixed TTM fluid 112 within the chiller tank 214 flows over the dam 228 and into the circulation tank 224. In other words, the mixing circuit 222 mixes the TTM fluid 112 within chiller tank 214 with the TTM fluid 112 within circulation tank 224 to cool the TTM fluid 112 within the circulation tank 224. A temperature sensor 225 within the circulation tank 224 measures the temperature of the TTM fluid 112 within the circulation tank 224. The temperature control logic may control the mixing pump 221 in accordance with temperature data from the temperature sensor 225 within the circulation tank 224.

The circulation tank 224 includes a heater 227 to increase to the temperature of the TTM fluid 112 within the circulation tank 224, and the heater 227 may be controlled by the temperature control logic. In summary, the temperature control logic when executed by the processor (see FIG. 3) may 1) receive temperature data from the temperature sensor 215 within the chiller tank and the temperature sensor 225 within the circulation tank 224 and 2) control the operation of the chiller 213, the chiller pump 211, the heater 227, and mixing pump 222 to establish and maintain the temperature of the TTM fluid 112 within the circulation tank 224 at the target temperature for the TTM therapy.

The circulation subsystem 230 includes a circulation pump 213 to pull TTM fluid 112 from the circulation tank 224 and through a circulating circuit 232 that includes the pad set 120 located upstream of the circulation pump 213. The circulating circuit 232 also includes a pressure sensor 237 to represent a pressure of the TTM fluid 112 within the pad set 120. The circulating circuit 232 includes a temperature sensor 235 within the circulation tank 224 to represent the temperature of the TTM fluid 112 entering the pad set 120 and a temperature sensor 236 to represent the temperature of the TTM fluid exiting the pad set 120. A flow meter 238 is disposed downstream of the circulation pump 213 to measure the flow rate of TTM fluid 112 through the circulating circuit 232 before the TTM fluid 112 re-enters that the circulation tank 224.

In use, the circulation tank 224, which may be vented to atmosphere, is located below (i.e., at a lower elevation than) the pad set 120 so that a pressure within the pad set 120 is less than atmospheric pressure (i.e., negative) when TTM fluid flow through the circulating circuit 232 is stopped. The pad set 120 is also placed upstream of the circulation pump 231 to further establish a negative pressure within the pad set 120 when the circulation pump 213 is operating. The fluid flow control logic (see FIG. 3) may control the operation of the circulation pump 213 to establish and maintain a desired negative pressure within the pad set 120. A supply tank 240 provides TTM fluid 112 to the circulation tank 224 via a port 241 to maintain a defined volume of TTM fluid 112 within the circulation tank 224.

Figure 3:
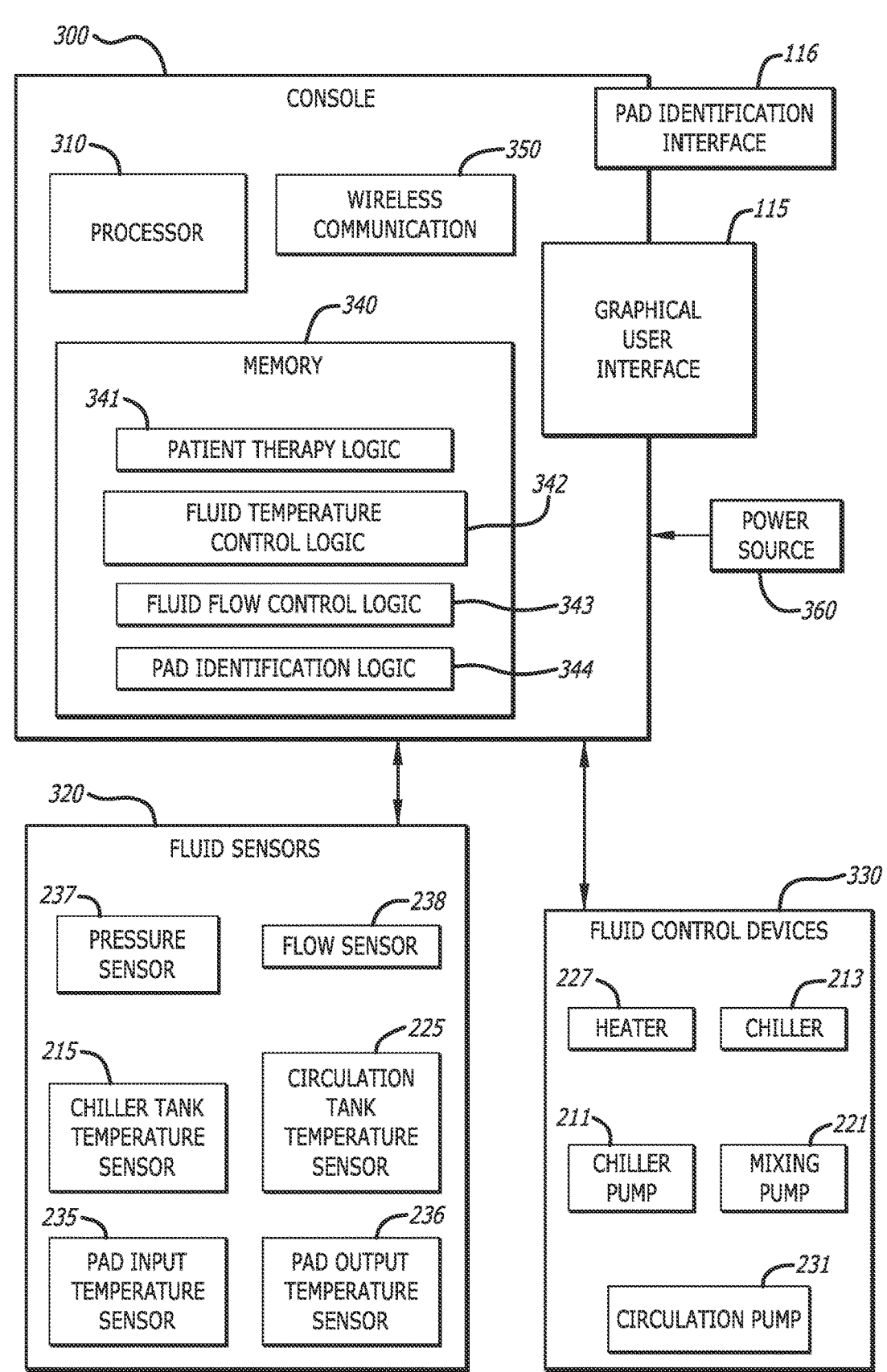
FIG. 3 illustrates a block diagram depicting various elements of a console of the TTM module of FIG. 1, in accordance with some embodiments.

FIG. 3 illustrates a block diagram depicting various elements of the TTM module 110 of FIG. 1, in accordance with some embodiments. The TTM module 110 includes a console 300 including a processor 310 and memory 340 including non-transitory, computer-readable medium. Logic modules stored in the memory 340 include patient therapy logic 341, fluid temperature control logic 342, fluid flow control logic 343, and pad identification logic 344. The logic modules when executed by the processor 310 define the operations and functionality of the TTM Module 110.

Illustrated in the block diagram of FIG. 3 are fluid sensors 320 as described above in relation to FIG. 2. Each of the fluid sensors 320 are coupled with the console 300 so that data from the fluid sensors 320 may be utilized in the performance of TTM module operations. Fluid control devices 330 are also illustrated in FIG. 3 as coupled with the console 300. As such, logic modules may control the operation of the fluid control devices 330 as further described below.

The patient therapy logic 341 may receive input from the clinician via the GUI 115 to establish operating parameters in accordance with a prescribed TTM therapy. Operating parameters may include a target temperature for the TTM fluid 112 and/or a thermal energy exchange rate which may include a time-based target temperature profile. In some embodiments, the fluid temperature control logic 342 may define other fluid temperatures of the TTM fluid 112 within the TTM module 110, such a target temperature for the TTM fluid 112 within the chiller tank 214, for example.

The fluid temperature control logic 342 may perform operations to establish and maintain a temperature of the TTM fluid 112 delivered to the pad set 120 in accordance with the predefined target temperature. One temperature control operation may include chilling the TTM fluid 112 within the chiller tank 214. The fluid temperature control logic 342 may utilize temperature data from the chiller tank temperature sensor 215 to control the operation of the chiller 213 to establish and maintain a temperature of the TTM fluid 112 within the chiller tank 214.

Another temperature control operation may include cooling the TTM fluid 112 within the circulation tank 224. The fluid temperature control logic 342 may utilize temperature data from the circulation tank temperature sensor 225 to control the operation of the mixing pump 221 to decrease the temperature of the TTM fluid 112 within the circulation tank 224 by mixing TTM fluid 112 from the chiller tank 214 with TTM fluid 112 within circulation tank 224.

Still another temperature control operation may include warming the TTM fluid 112 within the circulation tank 224. The fluid temperature control logic 342 may utilize temperature data from the circulation tank temperature sensor 225 to control the operation of the heater 227 to increase the temperature of the TTM fluid 112 within the circulation tank 224.

The fluid flow control logic 343 may control the operation of the circulation pump 231. As a thermal energy exchange rate is at least partially defined by the flow rate of the TTM fluid 112 through the pad set 120, the fluid flow control logic 343 may, in some embodiments, control the operation of the circulation pump 231 in accordance with a defined thermal energy exchange rate for the TTM therapy.

The console 300 may include or be coupled with a wireless communication module 350 to facilitate wireless communication with external devices. A power source 360 provides electrical power to the console 300.

The identification interface 116 may be coupled with the console 300 and provide pad identification data to the pad identification logic 344. The pad identification logic 344 may be configured so that, when executed by the processor 310, pad identification logic 344 may alert the clinician as to the identification of each thermal pad of the pad set 120. In an embodiment, the pad identification logic 344 may alert the clinician that one or more pads were not manufactured by a defined set of manufacturers. For example, if the identification interface 116 does not receive any pad identification data, the pad identification logic 344 may alert the clinician accordingly.

In some embodiments, the pad identification interface 116 may be configured to wirelessly receive pad identification data from the pad set 120. In the illustrated embodiment, the pad identification interface 116 may include a radio frequency identification (RFID) sensor configured to receive pad identification data from one or more RFID tags coupled with any or all pads of the pad set 120.

In some embodiments, the identification data may include a set of identification parameters (e.g., pad size), and the memory may include a corresponding set of identification parameters. An operation of the pad identification logic 344 may include comparing an identification parameter of the identification data with a corresponding identification parameter stored in memory, and the identification logic may be configured to modify the operation of the system in accordance with a result of the comparison.

Figure 4A:
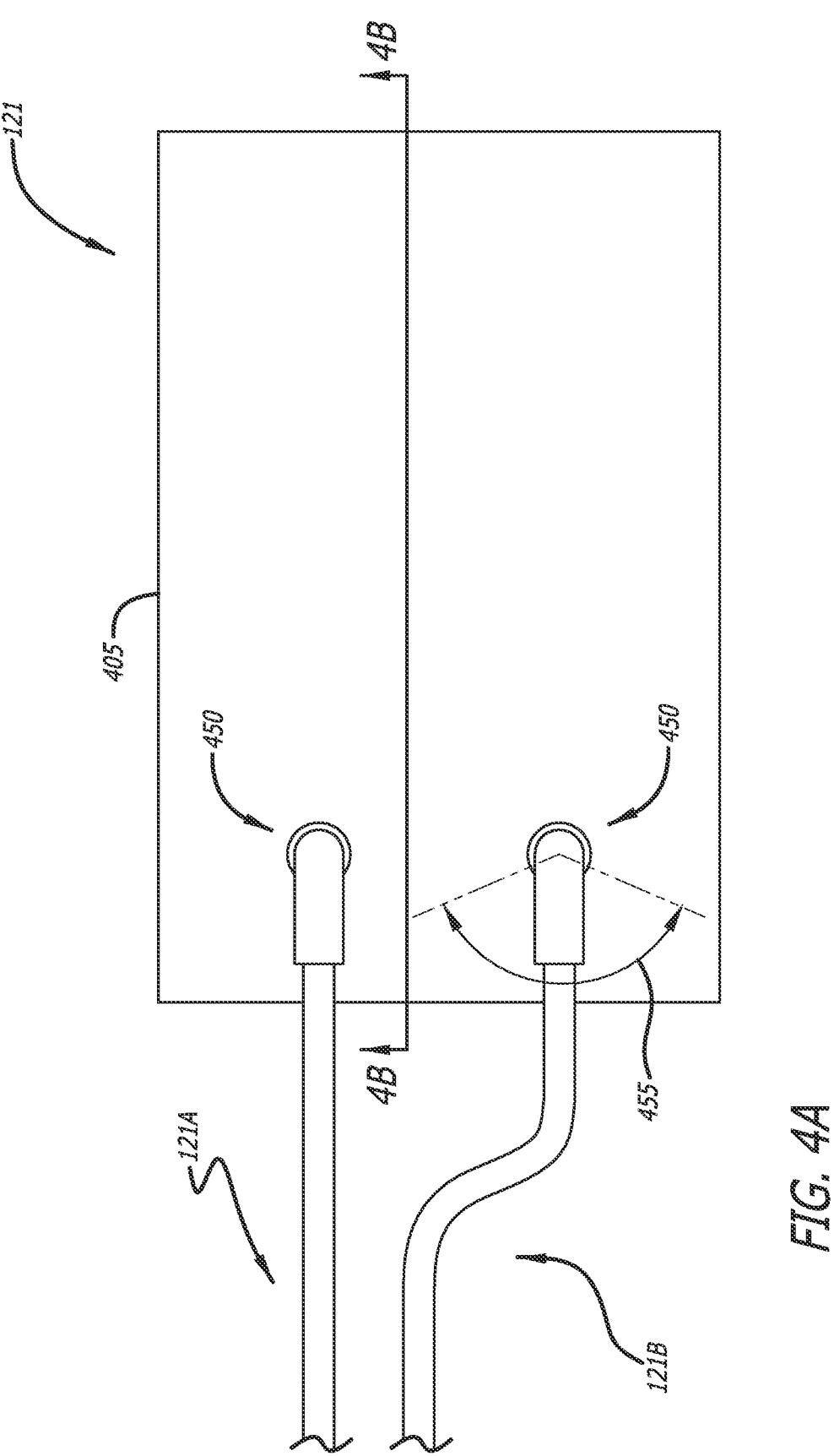
FIG. 4A is a top view of a thermal pad of the system of FIG. 1, in accordance with some embodiments.

FIG. 4A shows a top view of the thermal contact pad 121. While the description that follows describes features, components and details of the pad 121, the description that follows may equally apply to any and all other thermal contact pads of the pad set 120. The fluid delivery conduit 121A and the fluid return conduit 121B extend away from the joints 450, in accordance with some embodiments. As illustrated, the joints 450 may provide for a rotatable connection between fluid delivery conduit 121A and the fluid return conduit 121B and a pad portion 405 of the pad 121. The rotatable connection may provide for the fluid conduit to rotate through an angle 455 ranging up to about 90 degrees, 180 degrees, 360 degrees, or more. In some embodiments, the joint 450 may define a fixed rotatable connection, i.e., the joint may allow rotation but not separation. In other embodiments, the joint 450 may define a pre-assembled rotatable connection that allows rotation and separation by the clinician.

Figure 4B:
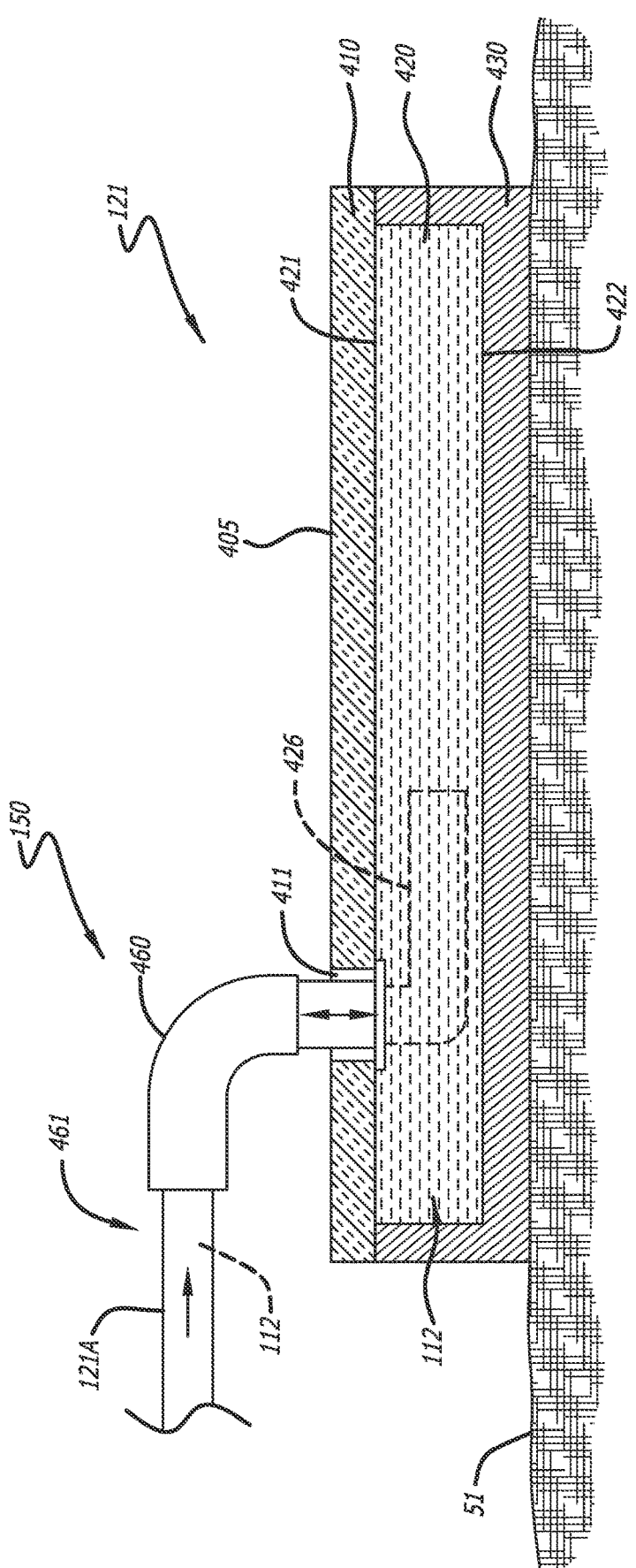
FIG. 4B is a cross-sectional view of the pad of FIG. 4A cut along sectioning lines 4B-4B, in accordance with some embodiments.

FIG. 4B shows a cross-sectional side view of the pad portion 405 of the thermal contact pad 121 of FIG. 4A in contact with the patient 50, in accordance with some embodiments. The pad 121 may include multiple layers to provide multiple functions of the pad 121. A fluid containing layer 420 is fluidly coupled with the fluid delivery conduit 121A via the joint 450 to facilitate circulation of the TTM fluid 112 within the fluid containing layer 420. Similarly, (although not shown in FIG. 4B) the fluid containing layer 420 is fluidly coupled with the fluid return conduit 121B via the joint 450. The fluid containing layer 420 having TTM fluid 112 circulating therein defines a heat sink or a heat source for the patient 50 in accordance with a temperature of the TTM fluid 112. The fluid delivery conduit 121A may also be coupled with an internal fluid conduit 426 of the fluid containing layer 420 so that TTM fluid 112 entering the fluid containing layer 420 passes through the internal fluid conduit 426.

The pad 121 may include a thermal conduction layer 430 disposed between the fluid containing layer 420 and the patient 50. The thermal conduction layer 430 is configured to facilitate thermal energy transfer between the fluid containing layer 420 and the patient 50. The thermal conduction layer 430 may be attached to the fluid containing layer 420 along a bottom surface 421 of the fluid containing layer 420. The thermal conduction layer 430 may be conformable to provide for intimate contact with the patient 50. In other words, thermal conduction layer 430 may conform to a contour of the patient 50 to inhibit the presence of space or air pockets between the thermal conduction layer 430 and the patient 50.

The pad 121 may include an insulation layer 410 disposed on the top side of the fluid containing layer 420. The insulation layer 410 is configured to inhibit thermal energy transfer between the fluid containing layer 420 and the environment. The insulation layer 410 may be attached to the fluid containing layer 420 along a top surface 422 of the fluid containing layer 420. In some embodiments, the insulation layer 410 may include one or more openings 411 extending through the insulation layer 410 to provide for coupling of the fluid delivery conduit 121A and fluid return conduit 121B with the fluid containing layer 420.

The joint 450 may include an elbow 460 to change the orientation of the fluid delivery conduit 121A. As shown, the orientation of 130 is shifted from an orientation that is perpendicular to the pad 121 to an orientation that is substantially parallel to the pad 121. The elbow 460 also establishes an orientation of a distal portion 461 of the fluid delivery conduit 121A to be substantially parallel to the pad 121 and/or the fluid containing layer 420.

Figure 5A:
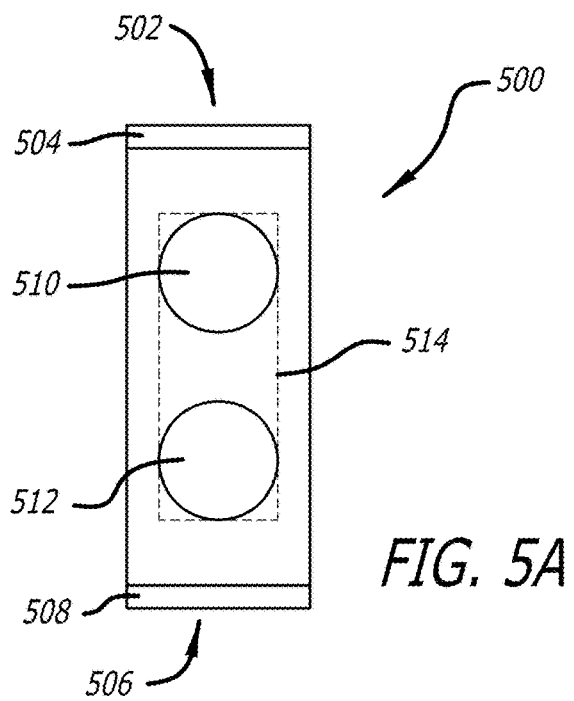
FIG. 5A is a front view of a pad connector of the system of FIG. 1, in accordance with some embodiments.

FIG. 5A shows a front view of a pad connector 500 of the system of FIG. 1, in accordance with some embodiments. The front view of the pad connector 500 illustrates a first (top) side 502 having a latch 504 and a second (bottom) side 506 having a latch 508. Further, the pad connector 500 includes one or more conduits 510, 512 and a flapper valve 514. In the embodiment of FIG. 5A, two conduits 510, 512 are shown where one of the conduits may be configured to receive TTM fluid from a fluid delivery conduit (e.g., of the FDL hub 600 of FIGS. 6A-6B) and the other conduit may be configured to return TTM fluid to a fluid return conduit (e.g., of the FDL hub 600 of FIGS. 6A-6B). However, in some embodiments, the pad connector 500 may include a single conduit such that multiple pad connectors are utilized where a first such pad connector is configured to delivery TTM fluid and a second such pad connector is configured to return TTM fluid.

Figure 5B:
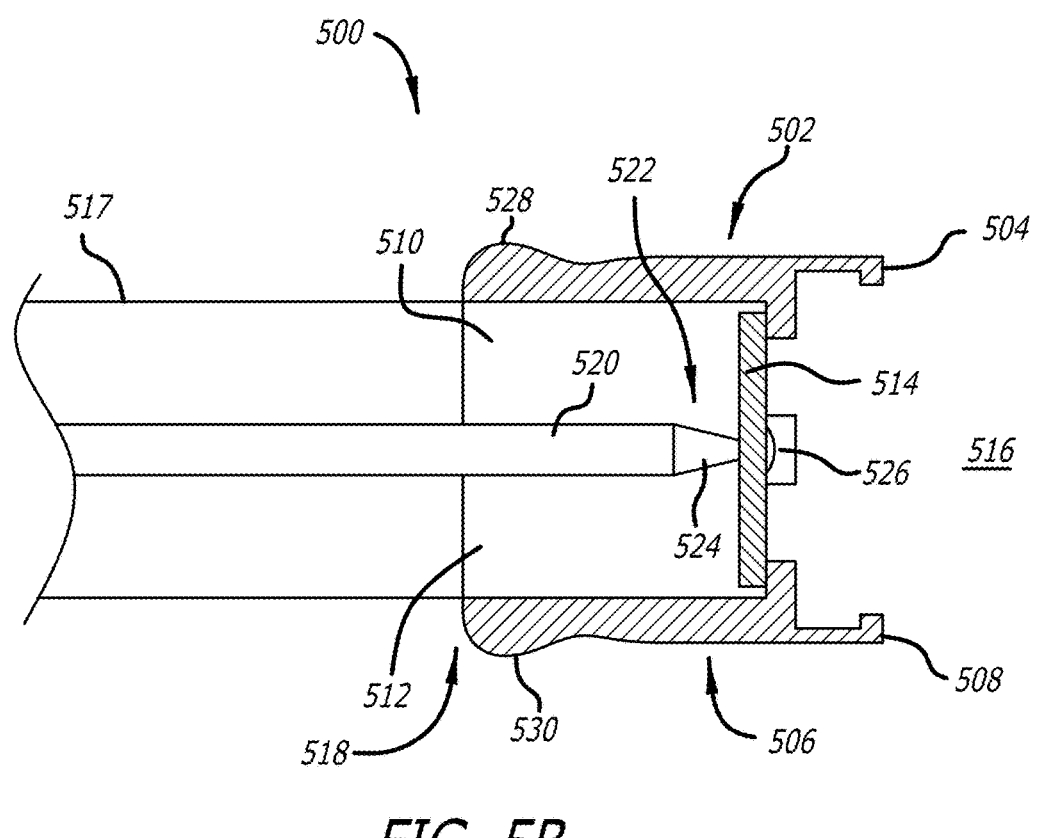
FIG. 5B is a side cross-sectional view of the pad connector of FIG. 5A, in accordance with some embodiments.

The flapper valve 514 is configured to block the openings of the conduits 510, 512 when in a closed state (as shown in FIGS. 5A-5B). The flapper valve 514 may be disposed within an interior of the pad connector 500 and be configured to deform when the pad connector 500 is coupled to a FDL hub (such as the FDL hub 600 of FIGS. 6A-6B). As is seen clearly in FIGS. 5A-5B and 7A-7C, the form of the flapper valve 514 alternates between a closed position (FIGS. 5A-5B, 7A) and an open position (FIGS. 7B-7C). When the pad connector 500 is disconnected from a FDL hub 600, the flapper valve 514 remains in a closed position (which may be a default position) where the flapper valve 514 blocks the openings of the conduits 510, 512 thereby preventing TTM fluid from leaking out of the pad to which the pad connector 500 is attached through the openings of the conduits 510, 512. In contrast, as seen in FIGS. 7B-7C, when the pad connector 500 is connected to a FDL hub 600, the flapper valve 514 is deformed into an open position. As seen in FIG. 7C, when in the open position, the flapper valve 514 does not block the opening of the conduits 510, 512, thereby allowing TTM fluid to pass therethrough.

In some embodiments, the flapper valve 514 may be a molded strip of rubber having a thickness of ⅟₁₆ inch, ⅛ inch, ¼ inch, etc.

FIG. 5B is a side cross-sectional view of the pad connector of FIG. 5A, in accordance with some embodiments. The cross-sectional view of FIG. 5B illustrates that latches 504, 508 extends proximally from a proximal end 516 of the pad connector 500 (e.g., toward a TTM module such as the module 110 of FIG. 1) and that tubing 517 extends distally from a distal end 518 of the pad connector 500 (e.g., toward a TTM pad such as the pad 121). FIG. 5B further illustrates that a conduit partition 520 is disposed within the connector 500 separating the conduits 510, 512, where the conduit partition 520 includes an aperture 522 in which the flapper valve 514 is disposed.

In some embodiments, the distal side of the aperture 522 may include a tapering 524 (e.g., a convex tapering) while a proximal side of the aperture 522 includes a tapering 526 (e.g., a concave tapering). Thus, the taperings 524, 526 assist the deformation of the flapper valve 514 (see FIGS. 7B-7C).

FIG. 5B also illustrates that the pad connector 500 may include compression strips 528, 530, where application of pressure on the compression strips 528, 530 causes movement of the latches 504, 508 in opposing directions (e.g., away from a FDL hub 600) thereby allowing the pad connector 500 to connect and disconnect from the FDL hub 600.

Figure 6A:
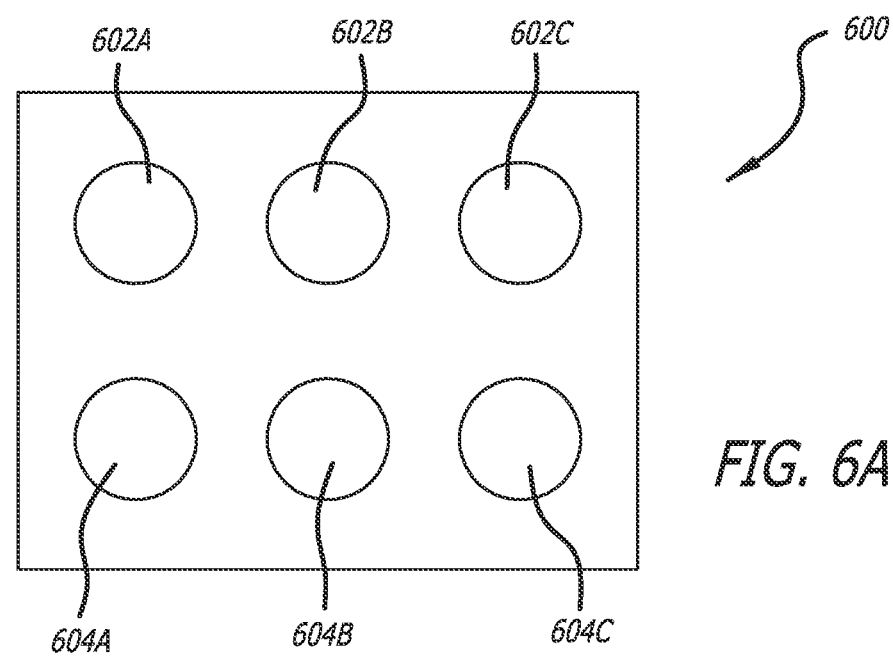
FIG. 6A is a front view of a fluid delivery line hub of the system of FIG. 1, in accordance with some embodiments.

FIG. 6A is a front view of a fluid delivery line hub, in accordance with some embodiments. The FDL hub 600 may be one specific embodiment of the FDL hub 131 of FIG. 1. The embodiment of the FDL hub 600 illustrated in FIG. 6A includes a plurality of first fluid conduits 602A-602C and a plurality of second fluid conduits 604A-604C, where one plurality may be configured to deliver TTM fluid to a first conduit of the pad connector 500 (e.g., the conduit 510) and the other conduit may be configured to receive TTM fluid from a second conduit of the pad connector 500 (e.g., the conduit 512). For instance, the plurality of first fluid conduits 602A-602C may deliver TTM fluid to the pad connector 500 while the plurality of second fluid conduits 604A-604C may receive return TTM fluid from the pad connector 500. It is noted that the number of conduits within each of the pluralities of the first and second fluid conduits 602A-602C, 604A-604C may differ from the illustration, which is not intended to be limiting.

Figure 6B:
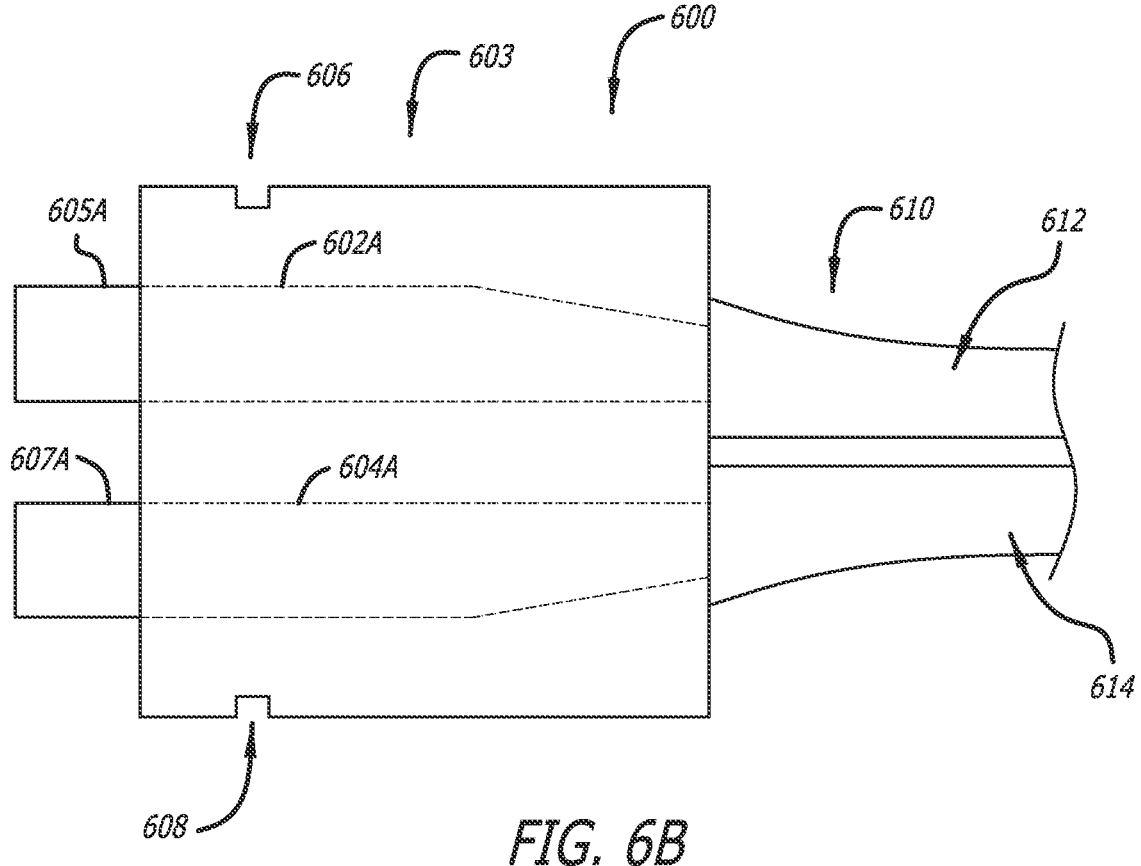
FIG. 6B is a side cross-sectional view of the fluid delivery line hub of FIG. 5A, in accordance with some embodiments.

FIG. 6B is a side cross-sectional view of the fluid delivery line hub 600 of FIG. 6A, in accordance with some embodiments. The cross-sectional view of the FDL hub 600 illustrates that the FDL hub 600 includes a housing 603 houses the plurality of first fluid conduits 602A-602C and the plurality of second fluid conduits 604A-604C. The housing 603 includes two grooves 606, 608 on opposing sides (e.g., on a top side and a bottom side). As is shown in FIGS. 7B-7C, the latches 504, 508 are disposed within the grooves 606, 608 when the pad connector 500 is connected to the FDL hub 600.

Additionally, the cross-sectional view of FIG. 6B illustrates that each conduit of both of the plurality of first fluid conduits 602A-602C and the plurality of second fluid conduits 604A-604C extend distally from the housing 603 (e.g., toward a TTM pad), where the distally-extending portion may be referred to as distal conduit tips (e.g., the distal conduit tips 605A, 607A). Further, the cross-sectional view of FIG. 6B illustrates tubing 610 that extends proximally from the housing 603 (e.g., toward a TTM module such as the module 110 of FIG. 1), where the tubing 610 may be comprised of a delivery tubing 612 and a return tubing 614. In some embodiments, each of the plurality of first fluid conduits 602A-602C may receive TTM fluid from the deliver tubing 612 and each of the plurality of second fluid conduits 604A-604C may return TTM fluid to the return tubing 614.

Figure 7A:
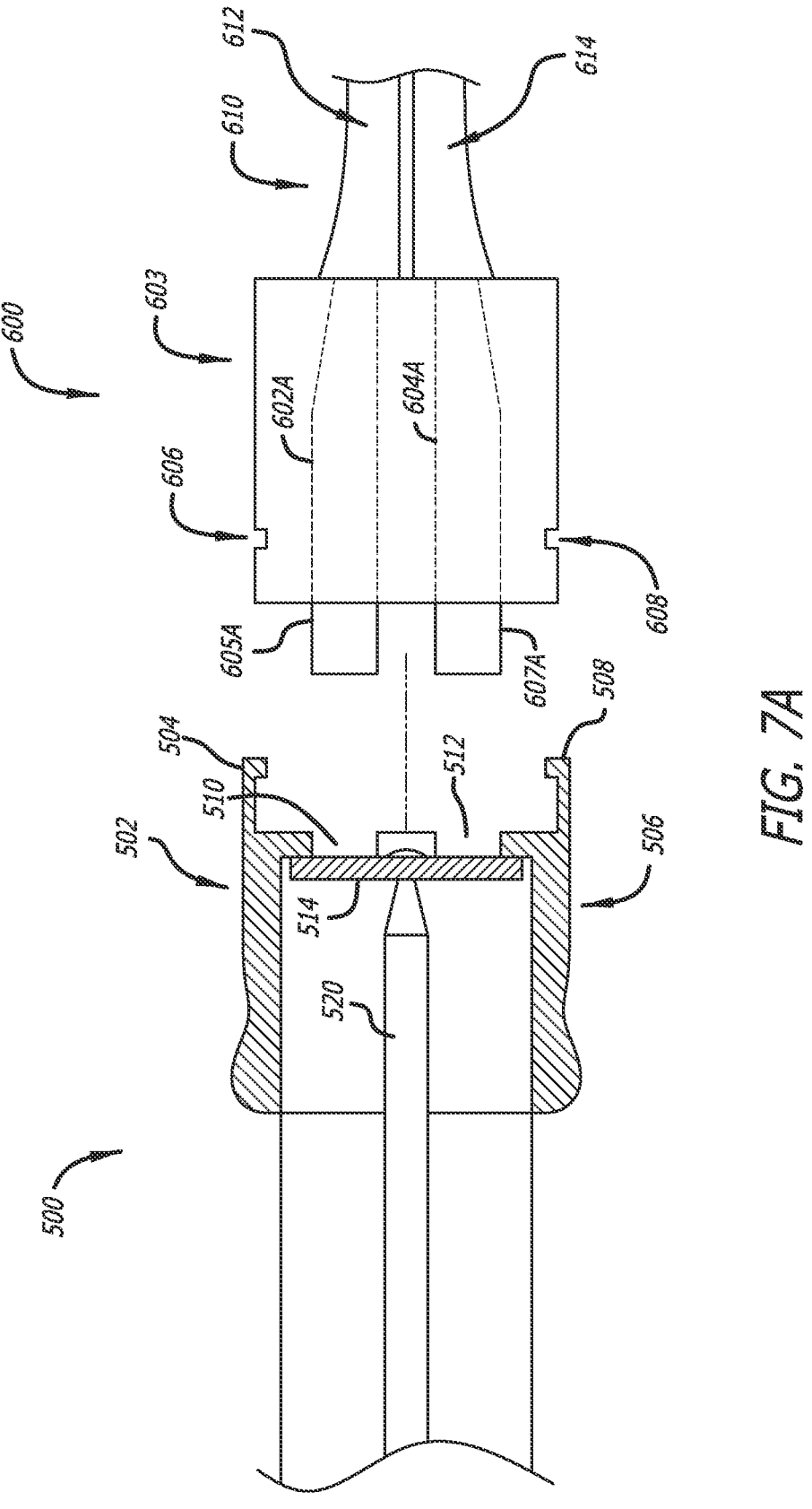
FIG. 7A is a view of a proximal portion of the pad connector of FIGS. 5A-5B approaching the fluid delivery line hub of the system of FIG. 1, in accordance with some embodiments.
Figure 7B:
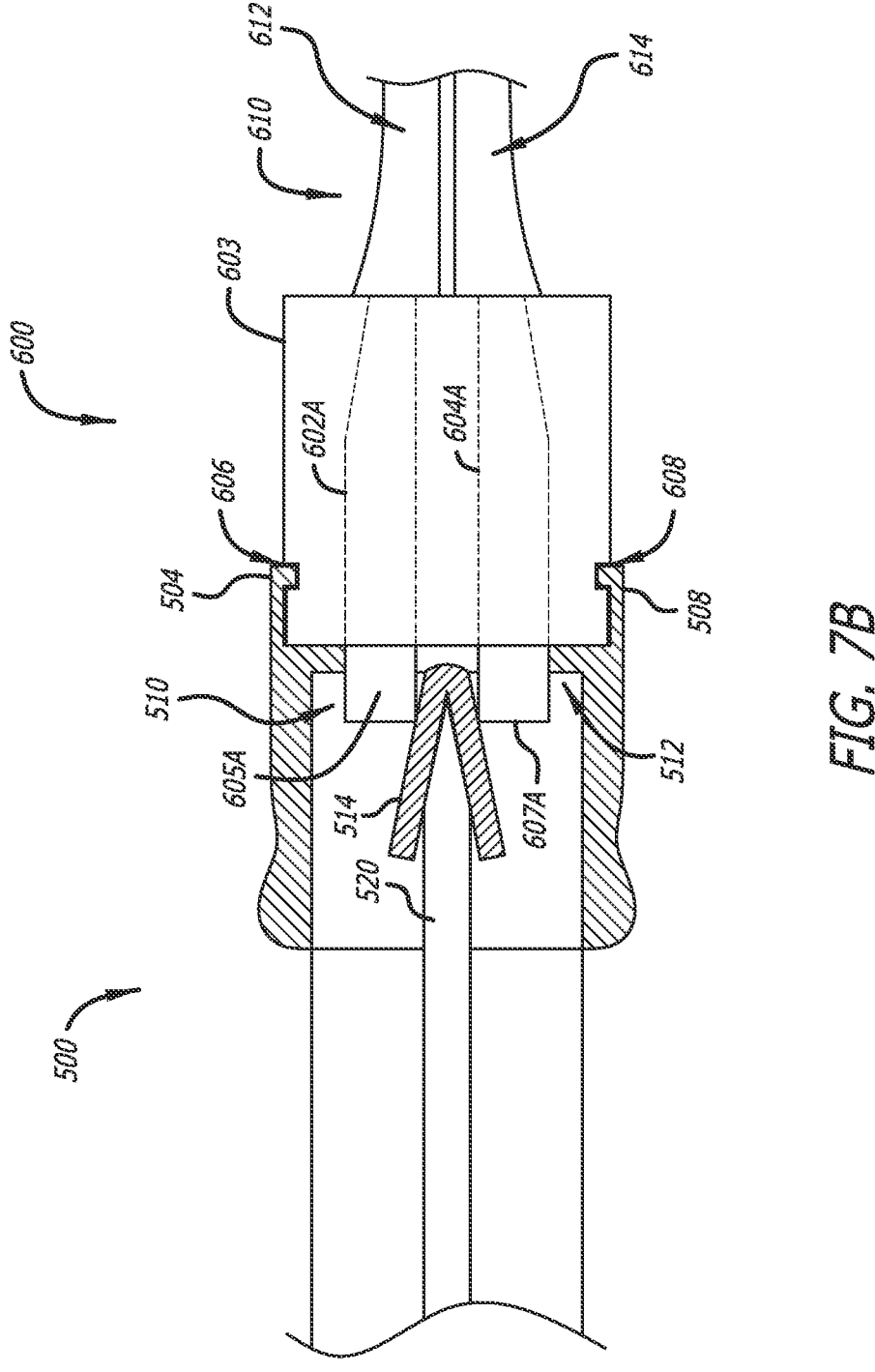
FIG. 7B is a view of the proximal portion of the pad connector and the fluid delivery line hub of FIG. 7A shown in a connected state, in accordance with some embodiments.
Figure 7C:
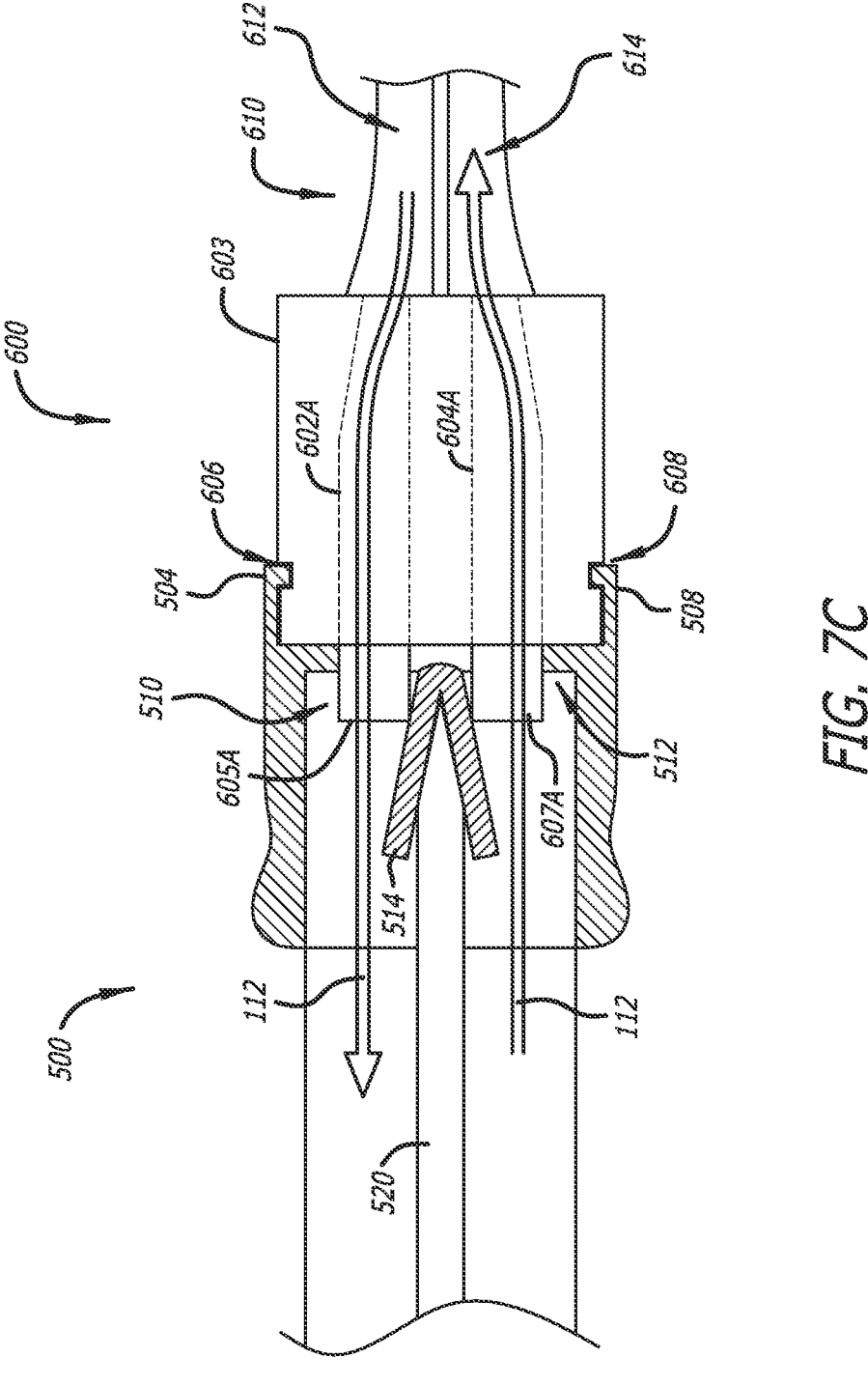
FIG. 7C illustrates the connected state of the proximal portion of the pad connector and the fluid delivery line hub of FIG. 7B having fluid flowing therethrough, in accordance with some embodiments.

FIG. 7A is a view of a proximal portion of the pad connector of FIGS. 5A-5B approaching the fluid delivery line hub of the system of FIG. 1, in accordance with some embodiments. FIG. 7A illustrates the pad connector 500 and the FDL hub 600 prior to connecting (or immediately following disconnecting) using a combination of the cross-sectional illustrations of FIGS. 5B and 6B. As is shown, the latches 504, 508 align with the grooves 606, 608 such that upon application of pressure to the compression strips 528, 530 of the pad connector 508, the latches 504, 508 will move in opposing directions allowing the pad connector 500 to physically connect with the FDL hub 600. As is understood, upon removal of the pressure from the compression strips 528, 530, the latches 504, 508 will return to a default position, which is within the grooves 606, 608 when the pad connector 500 is connected with the FDL hub 600. Further, the conduit 602A aligns with the conduit 510 and the conduit 604A aligns with the conduit 512 thereby providing for fluid communication between the pad connector 500 and the FDL hub 600. Notably, as the illustration of FIG. 7A shows the pad connector 500 and the FDL hub 600 in a disconnected state, the flapper valve 514 is shown in a closed position, e.g., covering the openings of the conduits 510, 512.

FIG. 7B is a view of the proximal portion of the pad connector and the fluid delivery line hub of FIG. 7A shown in a connected state, in accordance with some embodiments. As the pad connector 500 connects with the FDL hub 600, the distal conduit tips 605A, 607A enter the conduits 510, 512, respectively. Specifically, as the distal conduit tips 605A, 607A enter the conduits 510, 512, the flapper valve 514 is deformed (e.g., bent to form a curved or 'V' shape), which allows TTM fluid to flow between the conduits 602A, 510 and the conduits 604A, 512 (as seen in FIG. 7C).

FIG. 7C illustrates the connected state of the proximal portion of the pad connector and the fluid delivery line hub of FIG. 7B having fluid flowing therethrough, in accordance with some embodiments. As shown, TTM fluid may flow from the conduit 602A (from a TTM module) to the conduit 510 and from the conduit 512 to the conduit 604A such that FIG. 7C illustrates fluid communication. As is understood, when the pad connector 500 is disconnected from the FDL hub 600 (upon application of pressure to the compression strips 528, 530 and a pulling force to the pad connector 500 in the distal direction), the flapper valve 514 returns to its default (or non-deformed) shape thereby once again blocking the openings of the conduits 510, 512 (as seen in FIG. 7A).

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A targeted temperature management (TTM) system, comprising:
    a TTM module configured to provide a TTM fluid;
    a fluid delivery line (FDL) including a FDL hub, a fluid delivery lumen and a fluid return lumen; and
    a pad configured to facilitate thermal energy transfer between the TTM fluid and a patient, the pad comprising:
        a pad portion configured for placement on the patient, a fluid delivery conduit extending away from the pad portion, the fluid delivery conduit including a delivery conduit connector at a proximal end thereof,
        a fluid return conduit extending away from the pad portion, the fluid return conduit including a return conduit connector at a proximal end thereof, and
        a connector coupled to a distal end of each of the fluid delivery conduit and the fluid return conduit, the connector including a flapper valve configured to alternate between an open position and a closed position based on whether the connector is coupled with the FDL hub, wherein:
            the flapper valve includes a single deformable flapper member disposed within the connector,
            the single deformable flapper member defines a flat shape extending across both a delivery opening and a return opening of the connector in the closed position, and
            the coupling causes a protrusion of the FDL hub to displace the single deformable flapper member away from the delivery opening and the return opening, thereby deforming the single deformable flapper member away from the flat shape to a V-shape in the open position.

2. The system of claim 1, wherein the connector includes a connector housing having disposed therein proximal ends of the fluid delivery conduit and the fluid return conduit, a conduit partition separates the fluid delivery conduit, the fluid return conduit, and the flapper valve.

3. The system of claim 2, wherein the flapper valve is configured in the closed position for covering openings of each of the fluid delivery conduit and the fluid return conduit when the connector is uncoupled from the FDL hub.

4. The system of claim 2, wherein the connector is configured to receive the FDL hub upon coupling, causing the flapper valve to deform into the open position, wherein coupling the connector and the FDL hub establishes fluid communication therebetween.

5. The system of claim 4, wherein the flapper valve is configured to deform around the conduit partition.

6. The system of claim 2, wherein the conduit partition includes an aperture, and wherein the flapper valve is disposed in the aperture.

7. The system of claim 6, wherein each of a proximal side and a distal side of the aperture includes tapering to facilitate deformation of the flapper valve upon coupling of the connector and the FDL hub.

8. The system of claim 1, wherein the connector includes a top compression strip connected to a top latch and a bottom compression strip connected to a bottom latch, wherein each of the top latch and the bottom latch extends proximally from the connector.

9. The system of claim 8, wherein the top compression strip and the bottom compression strip are configured to cause movement of the top latch and the bottom latche in opposing directions upon application of pressure to the top compression strip and the bottom compressions strip.

10. The system of claim 1, wherein each of the fluid delivery lumen and the fluid return lumen include a distal conduit tip extending distally from the FDL hub.

11. The system of claim 10, wherein openings of the fluid delivery conduit and the fluid return conduit are configured to receive the distal conduit tip upon coupling the connector and the FDL hub.

12. A targeted temperature management (TTM) pad to receive and circulate TTM fluid to facilitate thermal energy transfer between the TTM fluid and a patient, the TTM pad comprising:

a pad portion configured for placement on the patient, a fluid delivery conduit extending away from the pad portion, the fluid delivery conduit including a delivery conduit connector at a proximal end thereof, a fluid return conduit extending away from the pad portion, the fluid return conduit including a return conduit connector at a proximal end thereof, and a connector coupled to a distal end of each of the fluid delivery conduit and the fluid return conduit, the connector including a flapper valve configured to alternate between the open position and the closed position based on whether the connector is coupled with a fluid delivery line (FDL) hub, wherein:

the flapper valve includes a single deformable flapper member disposed within the connector, the single deformable flapper member defines a flat shape extending across both a delivery opening and a return opening of the connector in the closed position, and the coupling causes a protrusion of the FDL hub to displace the single deformable flapper member away from the delivery opening and the return opening, thereby deforming the single deformable flapper member away from the flat shape to a V-shape in the open position.

13. The TTM pad of claim 12, wherein the connector includes a connector housing having disposed therein proximal ends of the fluid delivery conduit and the fluid return conduit, a conduit partition separates the fluid delivery conduit, the fluid return conduit, and the flapper valve.

14. The TTM pad of claim 13, wherein the flapper valve is configured in the closed position for covering openings of each of the fluid delivery conduit and the fluid return conduit when the connector is uncoupled from the FDL hub.

15. The TTM pad of claim 13, wherein the connector is configured to receive the FDL hub upon coupling, causing the flapper valve to deform into the open position, wherein coupling the connector and the FDL hub establishes fluid communication therebetween.

16. The TTM pad of claim 12, wherein the flapper valve is configured to deform around a conduit partition.

17. The TTM pad of claim 12, wherein a conduit partition includes an aperture, and wherein the flapper valve is disposed in the aperture.

18. The TTM pad of claim 17, wherein each of a proximal side and a distal side of the aperture includes tapering to facilitate deformation of the flapper valve upon coupling of the connector and the FDL hub.

19. The TTM pad of claim 12, wherein the connector includes a top compression strip connected to a top latch and a bottom compression strip connected to a bottom latch, wherein each of the top latch and the bottom latch extends proximally from the connector.

20. The TTM pad of claim 19, wherein the top compression strip and the bottom compression strip are configured to cause movement of the top latch and the bottom latche in opposing directions upon application of pressure to the top compression strip and the bottom compressions strip.

21. The TTM pad of claim 12, wherein upon coupling of the connector and the FDL hub, an opening of the fluid delivery conduit is configured to receive a distal conduit tip of the fluid delivery conduit and an opening of the fluid return conduit is configured to receive a distal conduit tip of the fluid return conduit.

* * * * *